US006187320B1

(12) United States Patent
Darai et al.

(10) Patent No.: US 6,187,320 B1
(45) Date of Patent: Feb. 13, 2001

(54) EQUINE HERPESVIRUSES (EHV) WHICH CONTAIN FOREIGN DNA, PROCESS FOR THE PREPARATION THEREOF AND THE USE THEREOF IN VACCINES

(75) Inventors: Gholamreza Darai, Heidelberg; Peter Thein, Oberzeitlbach; Walter Strube, Köln; Hanns Ludwig, Berlin, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 08/416,544

(22) Filed: Apr. 3, 1995

Related U.S. Application Data

(63) Continuation of application No. 07/858,291, filed on Mar. 26, 1992, now abandoned.

(30) Foreign Application Priority Data

Apr. 5, 1991 (DE) ................................. 41 10 962

(51) Int. Cl.$^7$ ..................... A61K 39/245; C07K 14/03; C12N 7/00
(52) U.S. Cl. ..................... 424/229.1; 435/235.1; 435/236; 435/320.1; 424/229.1; 530/350; 536/23.72
(58) Field of Search ................. 435/236, 235.1, 435/320.1; 424/229.1; 530/350; 536/23.72

(56) References Cited

U.S. PATENT DOCUMENTS

| 4,999,296 | * | 3/1991 | Ket et al. ..................... 435/235.1 |
| 5,187,087 | * | 2/1993 | Sondermeijer et al. ........... 435/172.1 |
| 5,223,424 | * | 6/1993 | Cochran et al. . | |

FOREIGN PATENT DOCUMENTS

| 0447303 | 9/1991 | (EP) . |
| 8704463 | 7/1987 | (WO) . |
| 9201045 | 1/1992 | (WO) . |

OTHER PUBLICATIONS

Fahey, K.J. Australian Biotechnology Conference, 8$^{th}$ Meeting p 129–133 (1988).*
Biotechnology Abstracts, Derwent Publications Ltd., London, GB. Abstract No. 91–05577, K.L. Fahey "Viruses as delivery vectors for vaccines—Recombinant vaccine production using a virus vector" & Aust. Biotechnol. Conf. 1989, 8 Meet., pp. 129–133.
Chemical Abstracts, vol. 98, No. 11, Mar. 14, 1983, Columbus, Ohio, US; Abstract No. 84274b, J. Staczek et al. "Genetic relatedness of the genomes of equine herpesvirus types 1, 2 and 3", p. 128 Col. 2; & J. Virol. 1983, vol. 45, No. 2, pp. 855–858.
Virology, vol. 173, No. 2, Dec. 1989, New York, US pp. 566–580, J.M. Colacino et al. "Physical structure and molecular cloning of equine cytomegalovirus DNA".

Chemical Abstracts article 116:52948y.
M. Gross–Bellard et al, Isolation of High–Molecular Weight DNA from Mammalian Cells, Eur.J. Biochem.36, pp.32–38 (1973).
J.Marmur, A procedure for the Isolation of Deoxyribonucleic Acid from Micro–organisms, J.Mol. Biol. (1961) 3, pp.208–218.
C.Gorman et al., HIgh Efficiency DNA–Mediated Transformation of Primate Cells Science, vol. 221, pp.551–553.
A. Ullrich et al., Rat Insulin Genes, Construction of Plasmids Containing the Coding Sequences, Science, vol. 196, pp. 1313–1319.
F.H.C. Crick et al., General Nature of the Genetic Code for Proteins, Nature, vol. 192, pp.1227–1232.
A.Twigg & D.Sherratt, Trans–complementably copy number mutants of plasmids ColE. Nature, vol. 283, pp.216–218.
G.F.Browning & M.J. Studdert, Physical mapping of a genome of equine herpesvirus 2 (equine cytomegalovirus), Arch.Virol. (1989) 104, pp. 77–86.
Peixuan Guo et al., Expression in Recombinant Vaccinia Virus of the Equine Herpesvirus 1 Gene Encoding Glycoprotein gp13 and Protection of Immunized Animals, Journal of Virology, Oct. 1989, pp.4189–4198.
C.W. Bell et al., Transcript analysis of the equine herpesvirus 1 glycoprein B gene homologue and its expression by a recombinant vaccinia virus, Journal of General Virology (1980), 71, 119–1129.
Peixuan Guo et al., Characterization of the gene and an antigenic determinant of equine herpesvirus type–1 glycoprotein 14 with homology to gB–equivalent glycoproteins of other herpesviruses , Gene, 87 (1990), 249–255.
J.M.Whalley et al., Identification and Nucleotide Sequence of a Gene in Equine Herpesvirus 1 analogous to the Herpes Simplex Virus Gene Encoding the Major Envelope Glycoprotein gB, J. gen.Virol (1989), 70, 383–394.
F. Sanger et al., DNA sequencing with chain–terminating inhibitors in proc.Natl. Acad.Sci.USA, vol. 74, No. 12, pp. 5463–5467.
J.M. Colacino et al., Physical Structure and Molecular Cloning of Equine Cytomegalovirus DNA, Virology 173, pp. 566–580 (1989).
Chang & Cohen, Cloning Vehicles derived from P15A Plasmid in J.Bacteriol., vol. 134 (1978), pp.1142–1156.
P.A.Sharp et al., Detection of Two Restriction Endonuclease Activities in Haemophilus parainfuenzae Using Analytical Agarose–Ethidium Bromide Electrophoresis in Biochemistry, vol. 12, No. 16, 1973, pp. 3055–3063.

(List continued on next page.)

Primary Examiner—Phuong T. Bui
(74) Attorney, Agent, or Firm—Joseph C. Gil; Godfried R. Akorli

(57) ABSTRACT

The invention relates to equine herpesviruses (EHV) which contain foreign DNA elements in addition to the genome sequences necessary for the replication thereof, to process for the preparation thereof and to the intermediates employed therein, and to the use thereof in vaccines against EHV infections.

9 Claims, 11 Drawing Sheets

OTHER PUBLICATIONS

Figure 1:
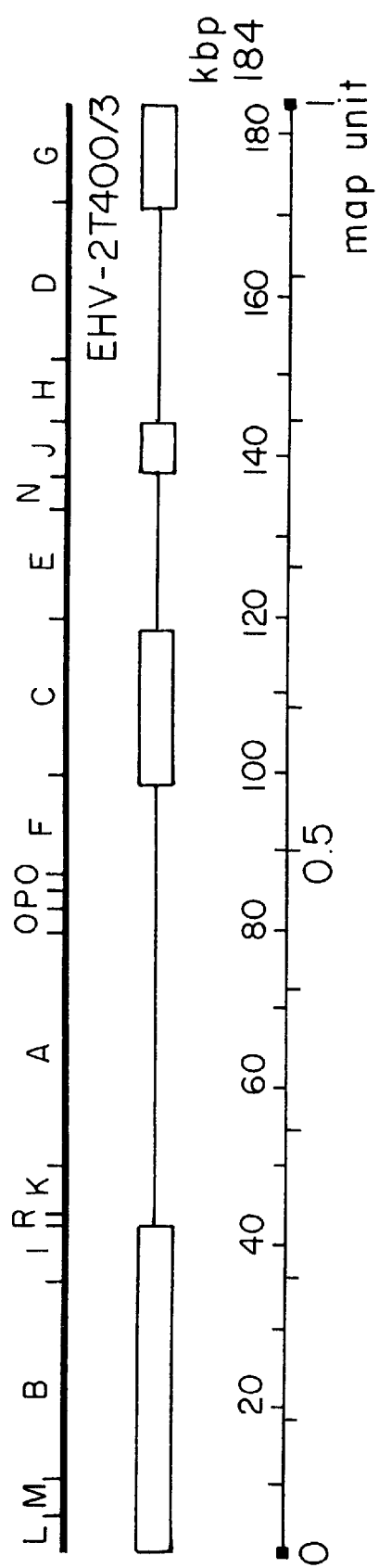

B.Perbal, A Practical Guide to Molecular Cloning, 1988.

C.W.Bell et al., Transcript analysis of the equine herpesvirus 1 glycoprotein B gene homologue and its expression by a recombinant vaccinia virus, Journal of General Virology (1990), 71, pp. 1119–1129.

P. W. Rigby et al., Labeling Deoxyribonucleid Acid to High Specific Activity In Vitro by Nick Translation with DNA Polymerase I, J. Mol. Biol. (1977) 113, 237–251.

H. Lehrach et al., RNA Molecular Weight Determinations by Gel Electrophoresis under Denaturing Conditions, a Critical Reexamination, Biochemistry, vol. 16, No. 21, 1977, 4743–4751.

V. Glisin, et al., Ribonucleid Acid Isolated by Cesium Chloride Centrifugation, Biochemistry, vol. 13, No. 12, 1974, 2633–2637.

Neubauer et al. Virology 227, 1997, p. 281–294.*

Browning et al. "Physical Mapping of a Genome of Equine Herpesvirus 2 . . . " Arch Virol 104, 1989, p. 77–86.*

Giphart–Gassler et al. "Studying DNA Mutations in Human Cells . . . " Mutation Research 214, 1989, p. 223–232.*

Cullinane, A.A., et al., 1988, J. Gen. Virol., 69: 1575–1590.

Elton, D.M., et al., 1991, Am. J. Vet. Res., 52: 1252–1257.

Nicolson, L., et al., 1990, J. Gen. Virol., 71:1793–1800.

Whalley, J.M., et al., 1981, J. Gen. Virol., 57: 307–323.

Bryans, J.T. et al., 1989, Herpesvirus Diseases of Cattle, Horses, and Pigs, Kluwer Academic Publishers, 176–229.

* cited by examiner

FIG. 4

```
              10          20          30          40          50
               |           |           |           |           |
   1   GAATTCCCCCCCTCCCGCTGCCTCTTAATATAACCCGTGTGGAGGGGGAT
  51   GCGACGGATGCCCCGAGCGGGCGGGCTCGCGCGCGCGCTCTCTATTGGCA
 101   AAACAAAAGCAGTAGGCAAGTAAACCCCGCTCCCCTCGAGCTCACCTGC
 151   AACCTCGCTTGTTGCAAAGATAGATGGAGTGCTGGGTGAGCTCAGCAGAG
 201   GCTATCCTCAATTCTTATGGAGGTGCAGTTTCCAGCTGAGGCCCATGGTC
 251   CTCGAGATGTGCCTCAGCATCCTATTTTTAGTTTTCTGTTTCTGTGAGC
 301   CACCGAAGAGAGAAAAGTCATAAAGTTGGCATTCCTTCCCAGCTCATCCA
 351   ATCGCACCTTCTTCTTGTCGCAGAGGATCTTGGGTATCAGGTTGCACTTC
 401   TTGTAGCCCAGGACCGCGCACTCGTGTTTGTTCTTGGTGTGGCTGATGAT
                                                  MstII
 451   CCTCTTGGAGAAGTCAAAGTATCCCCCCCTAGCGAGCCTGAGGACGGCGC
 501   GCACGTCCAGCCTCCCGAAGGAGGCGCACTCGTACAGGCACTCCAGGAAC
 551   CGCTTGGTATGGTCTGGATCTGGGCCTTGTTGCGCGTCTCCACCGTGGAG
 601   AAGATGGCGTTCTTGACCAGGTTGAGCCTGGCGCGCGGGTTGGTCAGTAT
 651   GGGCGCGGTCTCGCTGTAGACGCGAGCCACCAGCCCGGGGCCGTGCACCT
 701   TGGAGATGGTGGCGGTGGCCGCCTTGAACCAGGACACGTTGGAGCCCCTC
 751   TGGGTGGAGACTGGCCGAGGGGAAGTTGGTGGTCCAGAAGACGTCGCTCC
 801   TCCCCGGCGCACCAGCTGCTGGTTCTCCAGGCCCTGCAGGTCCAGGGTG
 851   GAGTTCCAGTTGGCCACGGAGATGGGAAAGACCGTGCGCACGGGCATGAA
 901   GCACTTGAGGTTGCCCACGGCGTAGAGGAAGGACAGGTAGTCCCCGCTGA
 951   TGTTCATGTTGATGGCCGTGCCGCTGGCGCACGCCGCGTCCGAGTAGAAC
1001   ACGCTCACGGTGAAGGAGGGCTCCTTCACGGAGTACTTTCTGATCACAAA
1051   GTTGTTGGTGAGCCGGGGGATGTCCATGACGGTGCGGTAGCGGGCGCCGC
1101   GGGGGTCGCACGCGATCTTGGTGTTGATGACCATGTTGGTGTTGAACACG
1151   TTGATCCCGAACCCGTGCACCGAGAGGCTGCTCACCGGGGCGAAGCTGTC
1201   TGCCAGGGGGCGCCGTCTCTCCCCCGACCCAAAGAGCGCCCCTCGCGGA
1251   GACCCAGCGGCAGCGTCATGGTGGCCCGGGTCTCCCGGGGGGCATGTACT
1301   TGCCCCTGTTGAGCAGGGAGACCAGTGCGTGGGCAGCCGGGCCCTCGCTC
1351   GAGGGCGGGCGCCTCGGACGGACGTGCCGCGCGCCCGGCCCATGGCCGCC
1401   AGACACATGGTGATCCTGTAGACGGCCATGCGCGGCGGGTACACGTACCA
1451   GCGCTCTACGCCGCCCCCTCCCTGGCGACCACCCTGCCCGGTCTGGCGC
1501   CGGGGTCCTTCTTGTAGACCGCCACCTTGAGATAGGGCATGGCCATGGTC
1551   ACGAGCGCCTGGTTCTCGTGAAAGCCCTCGGCCTCCAGGGAGATCT
```

EQUINE HERPESVIRUSES (EHV) WHICH CONTAIN FOREIGN DNA, PROCESS FOR THE PREPARATION THEREOF AND THE USE THEREOF IN VACCINES

This application is a continuation of application Ser. No. 07/858,291, filed Mar. 26, 1992, now abandoned.

The present relates to equine herpesviruses (EHV) which contain foreign DNA elements in addition to the genome sequences necessary for the replication thereof, to process for the preparation thereof and to the intermediates employed therein, and to the use thereof in vaccines against infections.

Herpes and influenza viruses as well as equine rhinoviruses, mammalian reoviruses, equine adenoviruses, mycoplasmas and bacteria such as, for example, streptococci and corynebacteria represent the main aetiological problems among the infectious respiratory disorders of horses. In addition to these, in the systemic infections there are arteritisvirus, salmonellae, *E. coli*. clostridia and, with colonisation on the intestine, rota- and coronaviruses. The aim is to develop effective vaccines which are tolerated and simple to use against these pathogens.

Equine herpesviruses are distributed enzootically in all horse-breeding areas of the world and are of predominant importance in the infectious diseases of horses. To date, a total of four equine herpesvirus serotypes have been indentified.

EHV-1 (Equine abortion virus), a pathogen belonging to the alpha-herpesviruses, previously called EHV-1 subtype 1 (rhinopneumonitisvirus), EHV-2 (Equine cytomegalo-like virus), a beta-herpes-virus, EHV-3 (Equine coital exantherma virus), belonging to the alpha-herpesviruses and EHV-4 likewise an alpha-herpesvirus, previously called EHV-1 subtype 2.

Equine herpesviruses cause economic losses in horse breeding throughout the world. These arise, in particular, owing to recurrent epidemics of abortion, respiratory disorders and, in some cases with a dramatic course, encephalitis. The economic importance of the losses during rearing, the missing of training and the losses of performance should not be underestimated.

Herpesviruses generally show only weak immunogenicity leading to a quantitatively small humoral immune response. Thus, for example, the respiratory form after EHV-4 infection frequently results in only a serologically weak humoral immune response. Currently employed in practice are predominantly monovalent EHV-1 live vaccines or inactivated EHV-1 vaccines, in some cases combined with heterologous antigens. Despite the use of these vaccines, clinical illnesses owing to infections with equine herpesviruses repeatedly occur. These may be monocausal illnesses due to herpesviruses of the various serotypes or consequences of mixed infections interacting with others of the said pathogens (factor illness).

Overall, the immunopreventative with the vaccines which can be employed at present is not yet satisfactory. It is therefore desirable to obtain equine vaccines which can be used without difficulty and confer a resilient immune protection against as many pathogens as possible.

Certain vector vaccines, based on apathogenic pathogens which, besides their genome sequences essential for propagation, contain foreign DNA coding for heterologous immunogens are known. It is also known that in some cases antigens of pathogenic pathogens have been inserted into avirulent pathogens, that is to say in vectors.

Alpha- and gamma-herpesviruses which contain foreign DNA, such as, for example, pseudorabies virus (Aujeszky virus) and the virus of Marek's disease and their use in vaccines are known (PCT Patent Application WO87/4463; WO89/1040). However, nothing is known about the use of equine herpesviruses, specifically beta-herpesviruses, such as EHV-2, as vectors for foreign DNA.

Alpha- and gamma-herpesviruses are fundamentally different in their biological behaviour and their structural organisation from the beta-herpesviruses. It is therefore not possible to draw any conclusions about beta-herpes-viruses from the behaviour of alpha- and gamma-herpes-viruses.

The present invention relates to:

1. Equine herpesviruses (EHV), in particular EHV Type 2, which, besides the genome sequences necessary for their replication, carry one or more foreign DNA elements.
2. Non-virulent or attenuated equine herpesviruses (EHV), in particular EHV Type 2, which, besides the genome sequences necessary for their replication, carry one or more foreign DNA elements.
3. Non-virulent or attenuated equine herpesviruses (EHV), in particular EHV Type 2, which, besides the genome sequences necessary for their replication, carry one or more foreign DNA elements which are located in their repetitive DNA sequences or in other genome sequences not necessary for their replication.
4. Equine herpesviruses according to 1, 2 and 3 (above) in which one or more segments in the genome sequences not necessary for their replication are absent, so-called deletion mutants.
5. Equine herpesviruses according to 1, 2, 3 and 4, which contain one or more foreign DNA sequences which code for proteins, and/or inactivate, owing to the insertion, the function of EHV genome sequences, and/or label the EHV genome at a required position.
6. Process for the preparation of the equine herpesviruses according to 1, 2, 3, 4 and 5 (above), characterised in that
   a) a gene bank for an EHV strain is established from genome fragments of this virus, and its physical genome map is constructed or, where appropriate, recourse is had to an existent gene bank, or to an isolated EHV DNA fragment,
   b) one or more insertion site(s) for the introduction of foreign DNA are identified in a manner known per se in the genome or on one or more genome fragments of this EHV strain, which fragments can be contained in plasmids or other vectors,
   c) where appropriate, one or more deletions are made in the genome or on one or more genome fragments with the insertion site(s) identified according to 6b) (above), it being possible for the genome fragments to be contained in plasmids or other vectors,
   d) foreign DNA elements are inserted in a manner known per se into the insertion site(s) identified according to 6b) (above) or into one or more regions from which deletion has been made according to 6c) (above), with the aim of constructing a so-called shuttle vector,
   e) where appropriate, the shuttle vector according to 6d (above) is co-transfected together with the genome of an equine herpesvirus in cells suitable for virus growth, or is transfected in separate steps, or the cells are transfected with the shuttle vector and infected with the equine herpesvirus,
   f) EHV virus recombinants which contain foreign DNA and are obtainable according to 6d) and e) are isolated and grown in a manner known per se.

Part steps b), c), d) can be carried out in any desired sequence.

7. Shuttle vector obtainable according to 6d (above).
8. Process for the preparation of the shuttle vector according to 7 (above), characterised in that one or more insertion site(s) for introducing foreign DNA elements are identified in a manner known per se in the genome or on one or more genome fragments of an EHV strain, which fragments can be contained in plasmids or other vectors, and, where appropriate, genome fragments which contain the identified insertion sites are inserted into known or newly constructed vectors, for example plasmid vectors, it being possible to insert where appropriate one or more deletions or single nucleotides or nucleotide sequences into the genome fragments either before or after insertion thereof into the vectors,
   and foreign DNA elements are inserted in a manner known per se into the identified insertion site(s) or into one or more regions from which there has been deletion.
   The stated part steps are carried out in any desired sequence.
9. Expression of genes based on the EHV according to 1, 2, 3, 4 and 5.
10. Vaccines based on the EHV according to 1, 2, 3, 4 and 5 (above)
11. Antigens, immunogens, translation units and epitopes which are prepared in vitro or in vivo with EHV according to 1, 2, 3, 4 and 5 (above).
12. Vaccines containing antigens, immunogens, translation units and epitopes according to 11 (above).
13. Use of EHV according to 1, 2, 3, 4 and 5 (above) as vaccines which allow differentiation of vaccinated from non-vaccinated, infected animals after immunisation.
14. Use of EHV according to 1, 2, 3, 4 and 5 (above) for the in vivo or in vitro preparation of antigens, immunogens, translation units, isolation thereof and use thereof in vaccines or diagnostic aids.
15. Use of antigens, immunogens, translation units and epitodes according to 11 (above) for the preparation of immune sera.
16. Use of EHV, in particular EHV-2, as vectors for foreign DNA elements.
17. Use of the shuttle vectors prepared according to 6.d) (above), which carry DNA sequences of EHV and DNA elements foreign for EHV, in particular the foreign DNA which has been inserted and reinserted again into these shuttle vectors, as DNA probes for detecting recombinant EHV which contain foreign DNA elements, where the foreign DNA in the shuttle vectors and in the recombinant EHV is at least partially identical.
18. Use of parts of the gene bank prepared according to 6.a) (above), which contain insertion site(s), identified according to 6.b), for introducing foreign DNA, as DNA probes for detecting possible insertion sites in the genome of EHV strains. to 6.a) for detecting EHV in biological sample material (pathogen diagnosis).
20. Use of oligonucleotides chemically synthesised on the basis of the determination of the nucleotide sequences of EHV genome fragments for detecting EHV in biological sample material (pathogen diagnosis).

The terms mentioned above have the following meaning:

Genome sequences necessary for the replication of EHV are parts of the complete genome of EHV which are indispensable for the growth of EHV, that is to say for the production of virus offspring. Localisation of some sequences is available only for a few herpesviruses and to an even smaller extent for EHV. It is necessary for the implementation of the present invention to leave these genome sequences necessary for replication unchanged, testable by whether the modified virus is able to produce infectious offspring.

Foreign DNA elements (foreign DNA) are

DNA sequences, for example foreign genes, which are not originally present in the EHV vector virus employed.

Foreign DNA is inserted into the vector virus for the following reasons:

1. for expression of the foreign DNA
2. for inactivation of functions of DNA sequences of the vector virus
3. for labelling of the vector virus The foreign DNA inserted differs, depending on these reasons. If the intention is to express foreign DNA according to (1), the inserted foreign DNA must carry at least one open reading frame which codes for the required foreign protein(s). The foreign DNA additionally contains, where appropriate, its own or foreign regulator sequences. The length of the inserted foreign DNA depends on ensuring the required function of the expressed protein. In general, the length is between 1-nucleotide and 20 kB, preferably between 0.5 and 15 kB.

Examples which may be mentioned are, genes for immunogens of equine herpesviruses of types 1 to 4, equine influenza viruses, rhinoviruses, adeno-viruses, mammalian reoviruses, mycoplasmas and bacteria such as, for example, streptococci and cornebacteria, furthermore arteritisvirus, rickettsia, salmonellae, clostridia, *E. coli*, rota- and coronaviruses. Immunogens of equine herpesviruses of types 1 to 4 can be the viral glycoproteins gB, gC and gD (D. W. Bell, D. B. Boyle, J. M. Whalley (1990) J. Gen. Virol. 71, 1119–1129; p-Guo, S. Goebel, S. Davis, M. E. Perkus, B. Languet, P. Desmettre, G. Allen, E. Paoletti (1989) J. Virol 63, 4189–4198; P. Guo (1990) Gene 87, 249–255; J. M. Whalley, G. R. Robertson, M. A. Scott, G. C. Hudson, C. W. Bell, L. M. Wordworth (1989) J. Gen. Virol. 70, 383–394), these names having been taken over from the nomenclature of HSV glycoproteins. Immunogens of the said pathogens can be the viral glycoproteins or membrane proteins of the other said pathogens.

If the intention is to inactivate DNA sequences according to (2), it suffices to interrupt the vector virus' own DNA sequence by, in principle, at least one foreign nucleotide. The maximum length of the foreign DNA inserted for the inactivation depends on the uptake capacity of the vector virus for foreign DNA. In general, the length of the foreign DNA is between 1 nucleotide and 20 kB, preferably between 0.1 and 15 kB.

If the intention is to insert DNA sequences for labelling according to (3), the length thereof depends on the detection method for identifying the labelled virus. In general, the length of the foreign DNA is between 1-nucleotide and 20 kB, preferably between 20 nucleotides and 15 kB.

Vector virus is an EHV, in particular EHV-2, which is suitable for insertion of foreign DNA and is able to transport the inserted foreign DNA in its genome into infected cells or organisms and thus makes possible expression of the foreign DNA therein.

Non-virulent EHV are
  viruses which do not lead to manifestation of clinical signs after natural or experimental infection of horses.
Attenuated EHV are
  viruses which have, owing to modification of their genome, become less or non-pathogenic or -virulent for horses.
Repetitive DNA sequences are
  sequences of nucleotide building blocks which occur repeatedly one after the other or scattered over the genome of EHV.
Genome sequences not necessary for replication of EHV are
  parts of the complete genome of EHV which are not necessary for the growth of EHV.
  These may be repetitive DNA sequences. These can also be sequences which would be essential for replication if they were not to occur repeatedly.
  These can also be DNA sequences which have in their nucleotide sequence no "open reading frame" for coding proteins and/or code in their nucleotide sequence for proteins which are non-essential for virus growth and/or have in their nucleotide sequence no sequences relevant for virus growth or DNA replication. It is necessary in every case to check the replicability of the potential vector virus after insertion and/or deletion has taken place.

Deletions are

DNA fragments absent from the genome of EHV.

Deletion mutants are variants of EHV which contain deletions in their genome.

Insertion mutants are variants of EHV which contain additional DNA sequences in their original genome sequences. Preferred variants are those into which additional DNA sequences have been inserted experimentally.

Gene bank is the totality of the fragments, contained in replicable vectors, of a genome.

It is obtained by fragmentation of the genome and insertion of all, some or most of the fragments into replicable vectors such as, for example, plasmids.

Genome fragment is a fragment of a genome which can occur in isolation or be inserted into a replicable vector.

Physical genome map is the assignment of restriction enzyme recognition sites to a DNA sequence, which is depicted in a straight line or circular diagram.

Physical genome maps of EHV-2 strains are known through "Physical Mapping of a Genome of Equine Herpesvirus 2 (Equine Cytomegalovirus)" Browning, G. F. and Studdert, M. J. (1989), Arch. Virol. 104, 77–86 and Virology 173 (1989), page 566–580, J. M. Colacino et al.

A physical genome map of the EHV-2 strain Thein400/3 is described hereinafter.

Suitable insertion sites are loci in a virus genome which are suitable for the uptake of foreign DNA.

They are identified, for example, by the following methods:

a) identification of potentially non-protein-coding sequences by determination of the nucleotide sequence of a viral DNA fragment, b) identification of potentially protein-coding regions whose proteins are inessential for virus growth, by determination of the nucleotide sequence of a viral DNA fragment c) identification of DNA sequences which are inessential for virus growth or its DNA replication, by determination of the nucleotide sequence of a viral DNA fragment, d) identification of repetitive sequences by, for example, DNA/DNA hybridisation and, where appropriate, nucleotide sequence analyses, e) modification of the genome sequences, for example by nucleotide exchange, deletion or insertion or of combinations thereof, f) any desired combination of a), b), c), d) and e), and subsequent checking of the significance of the potential isertion site for the replicability of the potential vector virus, the identified insertion site being termed suitable if growth of the recombinant vector virus is not prevented after insertion of foreign DNA into this site.

"Open reading frame" is a reading frame which is not interrupted by any stop codon. It is usual to check on the basis of the DNA sequence rather than the RNA sequence whether an open reading frame is present. Crick, F. H. C., L. Barnett, S. Brenner, and R. J. Watts Tobin, 1961. "General Nature of the Genetic Code for Proteins" Nature 192: 1227–1232.

Inactivation by insertion means that the inserted foreign DNA prevents the expression or function of EHV-intrinsic genome sequences.

Labelling by insertion means that the inserted foreign DNA makes it possible subsequently to identify the modified EHV.

Plasmids which can be employed according to 6b are, for example, bacterial plasmids. These are extrachromosomal DNA sequences in the form of a ring which are able to replicate in bacteria. These are known from "Molecular Cloning", A Laboratory Manual, 2nd Edition 1989, ed. J. Sambrook, E. F. Fritsch and T. Maniatis, Cold Spring Harbor Laboratory Press, particularly suitable examples are pBR322, pAT153, pUC18, pUC19, pACYC184. The manipulation of these plasmids is carried out by the methods indicated in the said literature.

Other vectors which can be employed according to 6b)

are, for example, bacteriophages, for example bacteriophage lambda.

Shuttle vectors are plasmids, in particular bacterial plasmids, which contain the foreign DNA which is to be inserted, flanked by DNA sequences of the vector virus. The preparation, replication and use thereof is described hereinafter.

Regulator sequences are

DNA sequences which influence the expression of genes. These are known from "Molecular Biology of the Gene", Watson, J. D.; Hopkins, N. H.; Roberts, J. W.; Steitz, J. A. and Weiner, A. M. 1987), The Benjamin/Cummings Publishing Company, Menlo Park. Those which may be mentioned as preferred are promoters such as, for example, the Rous sarcoma virus promoter (Gorman et al. (1983) Science 221, 551–553), the EHV-1 gB promoter (J. Gen. Virol. (1989), 70 383–394, Identification and Nucleotide Sequence of a Gene in Equine Herpesvirus 1, Analogues to the Herpes Simplex Virus gene Encoding the Major Envelope Glycoprotein gB, by J. M. Whalley, G. R. Robertson, A.

Scott, Grant C. Hudson, C. W. Bell and L. M. Woodworth, and Journal of General Virology (1990), 71 1119–1129, Transcript analysis of the equine herpesvorus 1 glycoprotein B gene homologue and its expression by a recombinant vaccinia virus, C. W. Bell, D. B. Boyle and J. M. Whalley) or the HSV-1 thymidine kinease promoter (McKnight (1980) Nucleic Acids Res. 8 5949–5963).

Transfection is
the introduction of DNA sequences, for example foreign DNA, which are contained in shuttle vectors or purified EHV DNA, into cells which are suitable for virus growth, with the aim of inducing virus recombinants which contain foreign DNA sequences. The cells suitable for virus growth can also be infected before or after the transfection with the vector virus in order to generate the virus recombinants which contain foreign DNA.

Co-transfection is
the simultaneous introduction of at least two different DNA sequences into cells which are suitable for virus growth, with the aim of inducing virus recombinants which contain foreign DNA sequences. The different DNA sequences are, on the one hand, foreign DNA, which can be incorporated in shuttle vectors, and, on the other hand, purified complete genome of the vector virus.

Methods for carrying out the transfection or co-transfection are known from "Methods in Virology Vol. VI" (1977), ed. K. Maramorosch, H. Koprowski, Academic Press New York, San Francisco, London. The method of the so-called calcium phosphate technique is preferred ("Methods in Virology Vol. VI" (1977), ed. K. Maramorosch, H. Koprowski, Academic Press New York, San Francisco, London).

Antigens are proteins or peptides whose expression is made possible by the foreign DNA in the vector virus and/or by the genome of the vector virus.

Immunogens are short-chain peptides or proteins which lead in the immunised organism to a homologenic protection from the clinical consequences of infection, and whose expression is made possible by foreign DNA and/or genome of the vector virus.

Translation units are translated amino-acid sequences, peptides or proteins.

Epitope is a specific binding site for antibodies based on an amino-acid sequence.

The equine herpesviruses (EHV) according to the invention according to 1, 2, 3, 4 or 5 (above) are prepared as indicated in 6 (above).

This specifically entails carrying out the following steps:

1. Selection of a suitable EHV strain.
2. Establishment of the viral gene bank of the suitable EHV strain.
3. Construction of the physical map of the viral genome of the suitable EHV strain.
4. Identification of potential insertion sites for foreign DNA in the genome of the suitable EHV strain.
5. Construction of a shuttle vector for transferring foreign genetic elements into the genome of the suitable EHV strain.
6. Construction of a recombinant EHV virus which contains foreign DNA and, for example, when it replicates expresses foreign protein.

Re 1.

Selection of a Suitable EHV Strain

All EHV types or strains are suitable in principle for use in the process according to the invention. EHV type 2 is preferred.

Particularly preferred strains of type 2 are those which can be grown to titres ≧$10^5$ PFu (Plaque Forming Unit)/ml in a tissue culture and can be prepared pure from the medium of the infected cells as extracellular, infectious virus.

The EHV-2 strain Thein-400/3, deposited in compliance with the Budapest Treaty on 24.7.1990 at the Institut Pasteur, C.N.C.M. under Reg. No. I-981, and its variants and mutants, has proved to be particularly suitable.

The viruses are grown in a conventional manner in tissue cultures of animal cells, for example in horse cells, monkey cells or rabbit cells, preferably in horse dermal cells such as the permanent horse dermal cell ED (ATCC CCL 57 or descendants thereof) or rabbit kidney cells such as in the rabbit kidney cell RK-13 (ATCC CCL37 or descendants thereof) or in monkey kidney cells.

The growing is carried out in a manner known per se in stationary, roller or carrier cultures in the form of united cell assemblages or in suspension cultures. Employed as growing media for the cells are all cell culture media known per se, for example described in the product catalogue of Flow Laboratoris GmbH Post 1249, 5309 Meckenheim, such as, in particular, the minimal essential medium (MEM) which contains as essential ingredients amino acids, vitamins, salts and carbohydrates, completed with buffer substances such as, for example, sodium bicarbonate or (hydroxyethylpiperazine-N-2-ethanesulphonic acid (herpes) and, where appropriate, animal sera such as, for example, sera from cattle, horses or the fetuses thereof. It is particularly preferable to use fetal calf serum in a concentration of 1–30% by volume, preferably 2–10% by volume.

The cells and cell lawns used to grow the viruses are grown in a conventional manner almost to confluence or to the optimal cell density. Before infection thereof with viruses, preferably the cell growth medium is removed and the cells are preferably washed with virus growth medium. Employed as virus growth media are, all cell culture media known per se, such as, in particular, the abovementioned MEM. Infection with a virus suspension is then carried out. The virus is present in the virus suspension in the virus growth medium in such a dilution that infection is carried out with an MOI (=multiplicity of infection corresponds to infectious virus particles per cells present) of 0.01–50, preferably 0.10–10.

The viruses are grown with or without the addition of animal sera. In the case were serum is employed, this is added to the growth medium in a concentration of 1–30% by volume, preferably 2–10% by volume.

Infection and virus growth are carried out at temperatures between room temperature and 40° C., preferably between 32 and 39° C., particularly preferably at 37° C. for several days, preferably until destruction of the infected cells is complete.

The virus-containing medium of the infected cells can be further processed, for example by removal of the cell detritus by means of filtration with pore sizes of, for example, 0.1–0.45 $\mu$m and/or centrifugation up to 10,000 g.

Filtrate or centrifugation supernatant can be used for virus concentration and purification. For this, filtrate or supernatant are subjected to a high-speed centrifugation until the virus particles have sedimented. Further purification steps by, for example, centrifugation in a density gradient can follow where appropriate.

Re 2.

Establishment of the viral gene bank

A defined gene bank is established from the genome of EHV, for example of the EHV-2 strain Thein-400/3, by the methods known per se from "Molecular Cloning", A Laboratoy Manual, 2nd Edition 1989, ed. J. Sambrook, E. F. Fritsch and T. Maniatis, Cold Spring Harbor Laboratory Press.

The genome is isolated and purified starting from the virus prepared and purified according to 1) above.

Native viral DNA is preferably extracted by treatment of the purified virions with aqueous solutions of detergents and proteases.

Detergents which may be mentioned are anionic, cationic, amphoteric, non-ionic detergents. Ionic detergents are preferably employed. Sodium dodecyl sulphate, sodium lauryl sulphate are particularly preferred.

Proteases which may be mentioned are, all proteases which operate in the presence of detergent, such as, for example, proteinase K. and Pronase. Proteinase K may be mentioned as preferred.

Detergents are employed in concentrations of 0.1–10% by volume, 0.5–3% by volume are preferred.

Proteases are employed in concentrations of 0.01–10 mg/ml of virus lysate, 0.05–0.5 mg/ml of virus lysate are preferred.

It is preferable to operate in aqueous buffered solution in the presence of DNase inhibitors. Buffer substances which may be mentioned are: salts of weak acids with strong bases such as, for example, tris(hydroxymethylaminomethane), salts of strong acids with weak bases such as, for example, primary phosphates or mixtures thereof.

The following buffer system may be mentioned as preferred: tris(hydroxymethylaminomethane).

The buffer substances or buffer systems are employed in concentrations which ensure pH values at which the DNA is not denatured. pH values of 5–9 are preferred, 6–8.5 particularly preferred, 7–8 very particularly preferred, operating in the neutral range may be mentioned in particular.

DNase inhibitors are, for example, ethylenediaminetetraacetic acid in concentrations of 0.1–10 Mmol, approximately 1 Mmolar is preferred.

The lipophilic components of the virus lysate are subsequently extracted. Used as extractants are solvents such as phenol, chloroform, isoamyl alcohol or mixtures thereof. It is preferable initially to employ a mixture of phenol and chloroform/isoamyl alcohol, the extraction being carried out in one or more stages.

Chloroform/isoamyl alcohol is preferably employed in the last stage of the extraction. It is alternatively possible to employ at first phenol and subsequently chloroform/isoamyl alcohol.

Further methods for the isolation of the viruses DNA are, for example, centrifugation of a virus lysate in a CsCl density gradient or in gel electrophoresis (Sharp et al. Biochem. 1973 (12) pp. 3055–3063).

The extraction of nucleic acids is described in "Molecular Cloning", A Laboratory Manual, 2nd Edition, 1989, ed J. Sambrook, E. F. Fritsch and T. Maniatis, Cold Spring Harbor Laboratory Press.

The DNA extracted in this way is preferably precipitated from the aqueous solution with, for example, alcohol preferably with ethanol or isopropanol and with the addition of monovalent salts such as, for example, alkali metal chlorides or acetates, preferably lithium chloride, sodium chloride or sodium acetate, potassium acetate.

The concentration of alcohol in this case is between 40 and 100% by volume, preferably between 60 and 80% by volume, particularly preferably about 70% by volume.

The chloride or acetate concentration is between 0.01 or 1 molar, preferably between 0.1 and 0.8 molar. If LiCl is employed, its concentration is between 0.1 and 1 molar, preferably between 0.4 and 0.8 molar.

Methods for the precipitation of nucleic acids are described in detail in "Molecular Cloning" loc. cit. The precipitated DNA is isolated from the aqueous suspension by, for example, centrifugation, preferably washed with alcohol, for example 70% by volume ethanol, and finally resolubilised in aqueous buffer solution.

A buffer substance which may be mentioned is tris-(hydroxymethyl)aminomethane in concentrations of 1–100 Mmol, 10–50 Mmol is preferred. Preferred pH values are 6–8.5, particularly preferably 7–8.

Further additives which may be mentioned are, for example, EDTA (ethylenediaminotetraacetic acid) in concentrations of 0.1–10 Mmolar, preferably 1–10 Mmolar.

An alternative possibility is also to resolubilise the precipitated DNA in 0.01 or 0.1×SSC buffer (Molecular Cloning) loc. cit. or in the ammonium carbonate buffer.

The viral DNA purified in this way is treated with restriction endonuclease in accordance with the manufacturers' instructions. Suitable restriction endonucleases are those which recognise at least one cleavage site specific for them on the viral genome. Examples of restriction endonucleases (restriction enzymes) are EcoRI, BamHI, SalI, HindIII, PstI, XbaI, AflIII or BspMII. The resulting DNA fragments are molecularly cloned by the methods described in "Molecular Cloning", A Laboratory Manual, 2nd Edition 1989, ed. J. Sambrook, E. F. Fritsch and T. Maniatis, Cold Spring Harbor Laboratory Press, into the corresponding recognition sequences of bacterial plasmid vectors, phages or cosmids. Particularly preferred for low molecular weight DNA fragments (up to about 15 kbp) are plasmid vectors, and for DNA fragments from about 15 kbp to about 45 kbp are cosmids.

Re 3.

Construction of the Physical Map of the Genome

The physical map of the viral genome, for example of the EHV-2 strain Thein-400/3, is subsequently constructed by means of methods known per se, for example DNA/DNA hybridisation, partial restriction with restriction endonucleases or double restrictions with restriction endonculeases (double digest), preferably using the viral gene bank, and DNA-DNA hybridisation.

The methods are known from "Molecular Cloning" loc. cit. or "A Practical Guide to Molecular Cloning 2nd, ed. B. Perbal, Wiley Interscience 1988.

Re 4.

The identification of suitable insertion sites is carried out in the genome or on virus genome fragments, for example by
a) identification of DNA sequences which do not code for proteins. For example by determination of the nucleotide sequence of the particular virus genome fragment, looking for nucleotide sequences which contain regions which do not code for proteins. The recognition sites located in these regions for restriction enzymes represent potential insertion sites. In order to establish whether a potential insertion site is a suitable insertion site in the complete genome of EHV, it is necessary to insert foreign DNA into the fragment and to incorporate the fragment with the insert into the viral genome. The recombinant virus containing foreign DNA is subsequently checked for replicability. If the recombinant virus containing foreign DNA grows, the recognition site identified above is suitable as insertion site.
b) Identification of DNA sequences which code for proteins which are inessential for virus growth, for example by determination of the nucleotide sequence and identification of "open reading frames" for inessential proteins. Proteins regarded as inessential proteins are those which are known from EHV and herpesviruses other than EHV and which have proved to be inessential for growth therein. It is assumed that such proteins, if they occur in EHV, are also inessential in EHV. The abovementioned nucleotide sequence of the EHV genome fragment is therefore investigated to find whether it contains an "open reading frame" for one of the inessential proteins known for other herpesviruses. Such proteins are possibly thymidine kinase, glycoprotein C, glycoprotein E (HSV nomenclature). In order to establish whether these potential insertion sites are suitable insertion sites in the complete genome of EHV, it is necessary to insert foreign DNA into the fragment and to incorporate the fragment with the insert into the viral genome. The recombinant virus containing foreign DNA is subsequently checked for replicability. If the recombinant virus containing foreign DNA grows, the recognition site identified above is suitable as insertion site.

c) Identification of DNA sequences which are inessential for DNA replication or virus growth. Such sequences are regarded as sequences of which it is known that they are inessential in EHV and/or herpesviruses other than EHV. This is carried out, for example, by comparative nucleotide sequence analysis of the EHV genome fragment. In order to establish whether these potential insertion sites are suitable insertion sites in the complete genome of EHV, it is necessary to insert foreign DNA into the fragment and to incorporate the fragment with the insert into the viral genome. The recombinant virus containing foreign DNA is subsequently checked for replicability. If the recombinant virus containing foreign DNA grows, the recognition site identified above is suitable as insertion site.

d) Identification of repetitive sequences by, for example, DNA/DNA hybridisation and subsequent identification of recognition sequences of restriction enzymes in these repetitive sequences, for example by nucleotide sequence analysis. The stated DNA/DNA hybridisation is carried out by, for example, hybridising genome fragments from the gene bank, which have been inserted into vectors, with the genome of EHV fragmented by restriction enzymes. The construction of the gene bank and the fragmentation must in this case have been carried out with the same restriction enzyme. The genome fragments which have been inserted into vectors and which hybridise with more than one fragment of the complete genome contain one or more repetitive sequences. In order to localise the repetitive sequence on the genome fragment, the nucleotide sequence is determined and compared with one another. Identical sequences on the fragment are repetitive. In order to establish whether a potential insertion site is a suitable insertion site in the complete genome of EHV, it is necessary to insert foreign DNA into the fragment and to incorporate the fragment with the insert into the viral genome. The recombinant virus containing foreign DNA is subsequently checked for replicability. If the recombinant virus containing foreign DNA grows, the recognition site identified above is suitable as insertion site.

e) Modification of the genome sequences, for example by nucleotide exchange, deletion or insertion or combinations thereof, f) any desired combination of a), b), c), d) and e).

Repetitive sequences are preferably localised by DNA/DNA hybridisation and characterised in detail by nucleotide sequence analyses.

The insertion sites must be suitable for the uptake of foreign DNA sequences of a length which depends on their abovementioned tasks.

Preferred insertion sites are those into which foreign DNA of a length of 1 nucleotide up to 15 kB can be inserted.

The capacity for uptake of foreign DNA can be increased by making deletions in the genome of the virus. The deletions have a size in the range from 1 nucleotide to 15 kB, preferably of 1–10 kB.

Re 5.

Construction of a shuttle vector for transferring foreign genetic elements.

Shuttle vectors are prepared for transferring foreign DNA into the vector virus by flanking the foreign DNA with DNA sequences of the vector virus. The construction is carried out in the following stages:

a) Isolation of the DNA sequence carrying the insertion site from the viral genome using restriction endonucleases and insertion thereof into a plasmid or a phage vector.

For this, the EHV is grown as indicated under 1 (selection of a suitable EHV strain) and purified as extracellular virus particle. The viral genome is isolated from this virus particle and fragmented as indicated under 2 (establishment of the viral gene bank).

The DNA fragments resulting from this are isolated from the separating gel (for example agarose gel) after the fractionation thereof, for example by electrophoresis, and the fragment which carries the identified insertion site is inserted into a plasmid or a phage vector.

Methods suitable for the fractionation of the DNA fragments are electrophoretic and chromatographic processes.

Gel filtration may be mentioned among the chromatographic processes.

Supports which may be mentioned in the electrophoretic processes are agarose or polyacrylamide. Examples of electrophoresis buffers which may be mentioned are ethylenediaminetetraacetic acid, phosphate/buffer (EPP) tris (hydroxymethyl)aminomethane borate ethylenediaminetetraacetic acid buffer (TBE) which has the following composition:

tris 10–100 mM, preferably 40–90 mM, particularly preferably 80–90 mM,
boric acid 10–100 mM, preferably 40–90 mM, particularly preferably 80–90 mM,
EDTA 1–10 mM, preferably 1–2.5 mM
pH 7–9, preferably 8–8.5 or tris(hydroxymethyl)aminomethane acetate ethylenediaminetetraacetic acid buffer (TAE) which has the following composition:
tris 10–100 mM, preferably 30–90 mM, particularly preferably 40 mM,
sodium
acetate 1–100 mM, preferably 5–50 mM,
EDTA 1–10 MM, preferably 1–2.5
pH 7–9, preferably 7.5–8.5.

A detailed list and description of electrophoresis buffers is described in
Current Protocols in Molecular Biology 1987–1988, published by Wiley-Interscience, 1987
A Practical Guide to Molecular Cloning, B, Perbal, $_2{}^{nd}$ edition published by Wiley-Interscience, 1988
Molecular Cloning, loc. cit.
Virologische Arbeitsmethoden (Working Methods in Virology), Volume III Gustav Fischer Verlag, 1989.

The procedure for the process is described in "Molecular Cloning" loc cit, or in Virolog. Arbeits-methoden Volume 3.

The DNA fragment with the insertion site is isolated from the support for example by electroelution of the support region containing the fragment. Alternatively by low-melting agarose processes (Molecular cloning loc. cit.) or by adsorption of the DNA fragment onto glass surfaces (Gene-clean® method).

For the insertion of the DNA fragment, double-stranded plasmid or phage vector DNA molecules are treated with restriction enzymes to produce the ends suitable for the insertion.

Examples of plasmids used are pAT153, pACYC184, pUC18/19, pBR322, pSP64/65.

Used as phage vectors are lambda phage variants such as, for example, -ZAP, -gt10/11 or phage M13mp18/19.

The restriction enzymes which can be employed are known per se, for example from Gene Volume 92 (1989) Elsevier Science Publishers BV Amsterdam.

The plasmid treated with restriction enzyme, or the phage vector is mixed with an excess of the DNA fragment to be inserted, for example approximately in the ratio 5 to 1, and treated with DNA ligases in order to bond the DNA fragment covalently end-to-end in the vector.

Ligases are enzymes which are able to link two DNA molecules via 3'-OH-5' radicals.

For the replication of the plasmids, the ligation mixture is introduced into pro- or eukaryotic cells, preferably into bacteria, and the latter are grown.

Examples of bacteria which are used are Escherichia coli strain K-12 and its derivatives, for example K 12–600 (Molecular cloning loc. cit.).

The preparation of the ligation mixture and of the bacterial culture is carried out in a manner known per se as described in Molecular cloning loc. cit.

The bacteria which contain plasmids with inserted foreign DNA are selected.

It is alternatively possible to employ an EHV DNA fragment which has already been inserted into a vector according to 2 (above) and which, according to 4 (above), contains an identified insertion site as starting material for preparing the shuttle vector.

b) Where appropriate, so-called "polylinkers" are inserted into the identified insertion site. For this, the EHV DNA fragment with the identified insertion site is treated with a restriction enzyme which opens the fragment at only one point. The fragment opened in this way is incubated with a polylinker and ligase for targeted insertion of other restriction enzyme recognition sites.

Polylinkers are DNA sequences which carry at least two restriction enzyme recognition sites connected together in sequence.

T4 DNA ligase may be mentioned as ligase, for example.

The polylinker is inserted either into the free DNA fragment or into the DNA fragment incorporated in plasmids or phage vectors.

If the polylinker is inserted into a free DNA fragment, the polylinker-containing fragment is subsequently inserted into plasmids, the plasmids are replicated in pro- or eukaryotic cells, preferably bacteria, and the latter are selected.

If the polylinker is inserted into DNA fragments which are contained in plasmids, the plasmids obtained in this way are replicated in pro- or eukaryotic cells, preferably bacteria, and selected.

c) Deletion of part sequences of the DNA fragment with the identified insertion site.

For this, the DNA fragment is treated with restriction enzyme, and the resulting fragments are fractionated. The fractionation is carried out by the methods described above.

d) Insertion of the foreign DNA into the insertion site.

The EHV DNA fragment with the identified insertion site is, either in free form or inserted into a plasmid, treated with one or more restriction enzymes which fractionate the fragment at the insertion site or in the inserted polylinker.

The foreign DNA is inserted into the recognition site by the methods known per se of sticky end or blunt end ligation using ligases. If the EHV fragment has been inserted, for example in a plasmid, the incubation mixture after the ligase reaction is introduced into pro- or eukaryotic cells, preferably bacteria, and the latter are grown and selected.

If the EHV DNA fragment before the insertion with foreign DNA is in free form, the DNA fragment with the insertion is inserted into a plasmid, introduced into pro- or eukaryotic cells, preferably bacteria (transformation), and the latter are grown and selected.

The abovementioned methods used for preparing the shuttle vector are described in detail in "Molecular Cloning", A Laboratory Manual, 2nd Edition 1989, ec. J. Sambrook, E. F. Fritsch and T. Maniatis, Cold Spring Harbor Laboratory Press.

Re 6.

Insertion of Foreign DNA into the Vector Virus Genome

The following processes are used to incorporate the foreign genetic element into the vector virus:

a) cotransfection of the shuttle vector DNA and of the native DNA of the vector virus into suitable host cells,
b) transfection of the shuttle vector DNA and infection with the vector virus into suitable host cells,
c) infection with the vector virus and transfection with the shuttle vector DNA into suitable host cells.

The methods of the processes suitable for this are described in "Methods in Virology Vol. VI" (1977), ed. K. Maramorosch, H. Koprowski, Academic Press New York, San Francisco, London. The preferred method is the so-called calcium phosphate technique ("Methods in Virology Vol. VI" (1977), ed. K. Maramorosch, H. Koprowski, Academic Press New York, San Francisco, London). Process a) is preferably employed. Necessary for this are the following steps:

1. Transformed cells which have been obtained by the processes described above and which contain shuttle vectors are grown and the shuttle vectors are isolated from the cells and further purified in a manner known per se. The purification is carried out, for example, by isopycnic centrifugation in a density gradient of, for example, CsCl.

The vector virus is grown and purified. The viral genome is extracted and further purified. The purification is carried out, for example, by isopycnic centrifugation in a density gradient of, for example, CsCl.

2. Circular or linearised shuttle vector DNA can be employed for the cotransfection. The linearised form is preferably employed.

The linearisation is carried out, for example, by treatment of the shuttle vector DNA purified in 1. by treatment with restriction endonucleases. Preferred restriction endonucleases permit the foreign DNA to be isolated in its entirety. Suitable in principle for this are all restriction endonucleases which have no recognition sequence in the foreign DNA.

3. The virus vector DNA and the shuttle vector DNA are mixed in the ratio 0.01 to $0.1 \times 10^{-12}$ molar vector virus DNA to 1 to 3×10⁻¹² molar shuttle vector DNA. The most suitable vector virus DNA:foreign DNA insert in the shuttle vector molecular ratio is 1:300

4. After the mixing of the DNA, the latter is coprecipitated with, for example, calcium phosphate and transferred to suitable cells (cotransfection) compare Molecular cloning loc. cit.

Suitable cells are animal cells, preferably mammalian cells, for example horse or rabbit cells, the permanent horse dermal cell line ED is particularly preferred (for example ATCC CCL57 or descendants thereof).

The mixed DNA can also be introduced into the cells by other methods.

The methods known per se with DEAE-dextran, or liposomes (for example Lipofectin®) or electroparation, may be mentioned.

5. The cells are cultivated by the methods described above (selection of a suitable EHV strain).

6. When a cytopathic effect occurs, the culture medium is removed, cell detritus is removed where appropriate by centrifugation or filtration and, where appropriate, storage and processing by the conventional methods of single-plaque purification of viruses are carried out.

7. The selection of recombinant vector viruses which contain foreign DNA is carried out, depending on the inserted foreign DNA, for example by:

a) expression of the foreign DNA with the aid of the recombinant vector viruses b) detection of the presence of the foreign DNA, for example by DNA/DNA hybridisations.

re a)

The expression of foreign DNA can take place at the RNA or protein level.

Expression of the foreign DNA at the protein level can be detected by, for example, infection of cells with the vector virus and subsequent immunofluorescence analysis with antibodies against the protein encoded by the foreign DNA or by immunoprecipitation with antibodies against the protein encoded by the foreign DNA from the lysates of infected cells.

Expression of the foreign DNA at the RNA level can be detected by hybridisation of the RNA from cells infected with vector virus with DNA which is at least in parts identical to the inserted foreign DNA.

re b.

For this purpose it is possible for the DNA to be obtained from the virus in question and to be hybridised with DNA which is at least in parts identical to the inserted foreign DNA.

8. The vector viruses which have been single-plaque purified and identified as recombinants are again checked for the presence and/or expression of the foreign DNA. Recombinant vector viruses which stably contain and/or express the foreign DNA are available for further use.

The figures represent the following:

FIG. 1

Physical map of the genome of EHV-2 strain Thein 400/3 for the restriction endonuclease EcoRI. The position of the repetitive DNA sequences which have been localised within the DNA sequences of the EcoRI DNA fragments B, C, G, I, J, L and M are indicated by black boxes. Map unit=genome coordinate; kbp=kilo base-pairs.

FIG. 2

Representation of the physical properties of the shuttle vector pX2-EH2-C1 (6.3 kbp) which harbours 3 kbp of the two terminal regions of the EcoRI DNA fragment C of the EHV-2 strain Thein 400/3 which is identified as SEQUENCE ID. NO. 6.

FIG. 3

Representation of the physical properties of the shuttle vector pEH2-EBt-X2 (4.6 kbp) which harbours 1956 bp of the right-hand terminus of the EcoRI DNA fragment B of the EHV-2 strain Thein 400/3 which is identified as SEQUENCE ID. NO. 7.

FIG. 4

DNA nucleotide sequence of the right flank of the EcoRI DNA fragment B of the EHV-2 strain Thein 400/3 between the recognition sites for EcoRI (genome coordinate 0.190; nucleotide position 1) and BglII (genome coordinate 0.189; nucleotide position 1596) which is identified as SEQUENCE ID. NO. 8.

FIG. 5

Representation of the physical properties of the recombinant plasmid pX2-EH2-C-LZ in which the LacZ casette (4440 bp) has been inserted into the HindIII and BamHI cleavage sites of the shuttle vector pX2-EH2-C1.

FIG. 6

Representation of the physical properties of the recombinant plasmid pEH2-EBt-LZ in which the LacZ casette (4440 bp) has been inserted into the HindIII and BamHI cleavage sites of the shuttle vector pEH2-EBt-X2.

FIGS. 7A and 7B

Microphotograph of ED-2 cell cultures which are infected with recombinant equine herpesviruses which express the bacterial β-galactosidase gene. Treatment of the cell cultures with 5-bromo-4-chloro-3-indolyl beta-D-galactoside (X-gal, 250 μg/ml) led to the development of blue plaques. The plaque morphology and the intensity of expression of the β-galactosidase gene are shown for the recombinant viruses EHV-2-B-Lac-7-231 and EHV-2-C-LacZ-658 in FIGS. 7A and 7B respectively.

FIG. 8

Gene for gB of EHV-1 cloned in pUC 19 (p19-EHV-1-GpB).

FIG. 9

Gene for gB of EHV-1 cloned in puC 19 modified by insertion of 2 DNA adaptors (p 19-EHV-1-gB-M4).

FIG. 10

Modified shuttle vector according to Example 7.4 pEH2-EB-LZ

FIG. 11

Modified shuttle vector according to Example 7.4 pEH2-EC-LZ

FIG. 12

Modified shuttle vector with inserted EHV-1 gB gene pEH2-EB-LZ+EH1 gB

FIG. 13

Modified shuttle vector with inserted pEH2-EC-LZ+EH1gB

EXAMPLES

Construction of EHV-2 Virus Recombinants

1. Preparation of the EHV-2 DNA 1.1. Cultivation of the EHV-2 strain Thein 400/3 on equine derm cells (ED) (ten) or more plastic culture bottles, 150 cm, 650 ml, supplied by Costar) at 37° C. for 4 to 6 days. Culture medium: E-MEM 2.0 g (Earle minimal esential medium 2.0 g $NaHCO_3$/l), 10% fetal calf serum (supplied by Flow) (Virol. Arbeitsmethoden Vol. 1, Gustav-Fischer Verlag, Stuttgart 1974, A. Mayr, O. A, Bachmann, B. Bibrack and G. Wittmann).

1.2. The supernatant from the infected cells was then centrifuged at 5,000 rpm in order to remove cell constituents.

1.3. The cell-free supernatant was ultracentrifuged (supplied by Beckmann) at 25,000 rpm (Beckmann SW-27 rotor) for 1 hour.

1.4. Virion pellet was resuspended in phosphate-buffered saline (PBS) (8 g NaCl, 0.2 g $H_2HPO_4$, 1.44 g $NaH_2PO_4$, 0.2 KCl, ad 1 l distilled water) or TNE (0.05 M tris, 0.1 M NaCl, 0.001 M EDTA, pH 7.2) and centrifuged over a sucrose cushion (30% aqueous sucrose buffered in TNE or buffered in PBS) at 25,000 rpm for 1 hour.

1.5. The virion pellet purified in this way was resuspended in 20 ml of TNE and adjusted with 2 ml of 10% sodium dodecyl sulphate (SDS) to a final concentration of 1% SDS. This treatment results in lysis of the virions.

1.6. Addition of 100 μg/ml proteinase K (supplied by Boehringer) and incubation at 37° C. for 1 hour (Gross-Bellard et al., 1973, Eur. J. Bioch. 36: p. 32).

1.7. Extraction of the DNA by extraction twice with phenol and subsequently chloroform/isoamyl alcohol by the method of Marmur (1961, J. Mol. Biol. 3: p. 208).

1.8. Supernatant was adjusted with 8 M potassium acetate solution to a concentration of 0.8 M potassium acetate, and then 3 times the volume of absolute ethanol (<−20° C.) was added. The ethanol DNA extract solution was left at −20° C. overnight and then centrifuged at 6,000 rpm at −20° C. for 30 min.

1.9. After decantation of the supernatant, the DNA pellet was dissolved in 0.01 or 0.1×SSC (1×SSC consists of: 0.15 M NaCl, 0.015 M Na citrate, pH 7.2).

1.10 Determination of the purity and of the concentration of the DNA was carried out by photometric measurement of the absorption at 2600 nm and 280 nm wavelength.

1.11 Storage of the DNA at 4° C.

2. Establishment of the EHV-2 Gene Bank

A defined gene bank of the EHV-2 strain Thein 400/3 which harbours the entire viral DNA sequences was established for the restriction endonucleases EcoRI, HINDIII and BamHI.

2.1. Restriction of 10 μg of the EHV-2 DNA with the restriction endonuclease EcoRI (supplied by Boehringer, 20U/μg) under the conditions specified by the manufacturer.

2.2. Fractionation of the resulting fragments in agarose (supplied by BRL) gel electrophoresis ((80 V, 20 h, 4° C.) by the method of Sharp et al. (1973, Biochem. 12: 3055–3063).

2.3. Staining of the gel with ethidium bromide (5 μg/ml) and visualisation of the DNA fragments under UV light. Preparation of the DNA fragments by cutting out the 18 resulting DNA bands (EHV-2 EcoRI DNA fragments A to R) from the agarose gel.

2.4. Electroelution of the DNA fragments as described by Sambrook, Fritsch and Maniatis (1989), Molecular Cloning, Cold Spring Harbor, N.Y. Storage at −20° C.

2.5. Restriction of 0.1 picoMole ($6 \times 10^{10}$ molecules) of the DNA of the plasmid vector pACYC184 (Chang and Cohen, 1978, K. Bacteriol. 143:1141) with the restriction endonuclease EcoRI. Subsequently treatment with alkaline phosphatase (supplied by Boehringer) as described by Sambrook, Fritsch and Maniatis (1989), Molecular Cloning, Cold Spring Harbvor, N.Y.

2.6. Ligation of the individual EHV-2 EcoRI DNA fragments with the DNA, treated with EcoRI and alkaline phosphatase, of the plasmid vector pACYC184 with the addition of 2U of T4 DNA ligase (supplied by Boehringer) as described by Sambrook, Fritsch and Maniatis (1989), Molecular Cloning, Cold Spring Harbor, N.Y.

2.7. Transformation of competent E. coli C600 cells with the ligation mixture and selection of the transformed bacterial colonies for the tetracycline resistance as described by Sambrook, Fritsch and Maniatis (1989), Molecular Cloning, Cold Spring Harbor, N.Y.

2.8. Cultivation, purification and characterisation of the recombinant plasmids which contain the EHV-2 EcoRI DNA fragments A to R as described by Sambrook, Fritsch and Maniatis (1989), Molecular Cloning, Cold Spring Harbor, N.Y.

3. Construction of the Physical Map of the Viral Genome

The physical map of the viral genome of EHV-2 strain Thein 400/3 (FIG. 1) was constructed by means of partial treatment of the DNA with the restriction endonuclease EcoRI and end-labellings and DNA/DNA hybridisations using the viral gene bank described by Grossmann and Moldave (1989), in: Methods in Virology, ed. S. P. Colowick and N. O. Kaplan, Academic Press, N.Y., and by Sambrook, Fritsch and Maniatis (1989), Molecular Cloning, Cold Spring Harbor, N.Y., (FIG. 1). The genome coordinates of each of the DNA fragments are listed in Table 1.

TABLE 1

Size of the EcoRI DNA fragments of the genome of EHV-2 strain Thein 400/3

| DNA Fragment | Size (kbp) | Genome coordinates |
|---|---|---|
| A | 30 | 0.266–0.429 |
| B | 25 | 0.054–0.190 |
| C | 20 | 0.537–0.646 |
| D | 20 | 0.822–0.932 |
| E | 14 | 0.646–0.717 |
| F | 12.5 | 0.469–0.537 |
| G | 12.4* | 0.932–1 |
| H | 8.2 | 0.770–0.822 |
| I | 6.8 | 0.190–0.228 |
| J | 6.8 | 0.741–0.779 |
| K | 6.8 | 0.236–0.266 |
| L | 5.1* | 0. –0.027 |
| M | 5.1 | 0.027–0.054 |
| N | 4.3 | 0.717–0.741 |
| O | 2.7 | 0.420–0.445 |
| P | 2.35 | 0.445–0.458 |
| Q | 1.0 | 0.458–0.469 |
| R | 1.4 | 0.228–0.236 |
| Total: | 183.45 | |

*Terminal fragments

4. Characterisation of the Repetitive DNA Sequences of the Viral Genome

The repetitive DNA sequences of the viral genome of EHV-2 strain Thein 400/3 were localised as described by Grossman and Moldave (1980), in: Methods in Virology, ed. S. P. Colowick and N. O. Kaplan, Academic Press, N.Y., and Sambrook, Fritsch and Maniatis (1989), Molecular Cloning, Cold Spring Harbor, N.Y., by DNA/DNA hybridisations using the viral gene bank in the EcoRI DNA fragments B, C, G, I, J, L and M. The positions of these repetitive DNA sequences are depicted in FIG. 1.

5. Construction of the Shuttle Vector for Transferring Foreign Genetic Elements into the EHV-2 Genome Two shuttle vectors pX2-EH2-C1 (FIG. 2) and pEH2-EBt-X2 (FIG. 3) were constructed to insert foreign genetic information into the EHV-2 genome. The two shuttle vectors have a bacterial plasmid portion of pAT153 (Twigg and Sheratt (1980) Nature 283: 216–19) and a viral portion of 3 kbp of the DNA sequences of the EcoRI DNA fragment C (pX2-EH2-C1) and 1.6 kbp of the DNA sequences of the EcoRI DNA fragment B (pEH2-EBt-X2) respectively.

5.1. re Shuttle vector pX2-EH2-C1:

The viral insert of the shuttle vector pX2-EH2-C1 contains the DNA sequences of the two terminal regions of the EcoRI DNA fragment C which are bounded by a recognition sequence of the restriction endonuclease BglII. The restriction endonuclease BglII separates the two terminal regions into two halves 1.4 and 1.6 kbp in size respectively. A polylinker (BglII-HindIII-BamHI-BglII) was inserted at this BglII cleavage site to make it possible to insert foreign genetic elements (see FIG. 2). The construction of the shuttle vector pX2-EH2-C1 was carried out in the following steps. The methods used are described in detail in Sambrook, Fritsch and Maniatis (1989), Molecular Cloning, Cold Spring Harbor, N.Y.

5.1.1. Molecular cloning of the EcoRI DNA fragment C (20 kbp; genome coordinates 0.537–0.646) into the bacterial plasmid vector pACYC184 and establishment of the recombinant plasmid pyEH2-E-C.

5.1.2. Restriction of the DNA of the recombinant plasmid pyEH2-E-C with the restriction endonuclease BglII. Since no BglII cleavage sites are present within the DNA sequences of pACYC184, this treatment results in deletion of those DNA sequences within the EcoRI DNA fragment C which are bounded by the outer BglII cleavage sites. Subsequently ligation of the DNA of the deleted recombinant plasmid.

5.1.3. Isolation of the insert of the deleted recombinant plasmid and molecular cloning into the bacterial plasmid vector pAT153 into which a DNA linker with the cleavage sites for XbaI-EcoRI-XbaI has been inserted within the recognition sequences for EcoRI and BamHI (pAT153 nucleotis position 3 to 375), the original cleavage sites for EcoRI and BamHI having been eliminated. Establishment of the recombinant plasmid pEH2-E-C.

Figure 2:
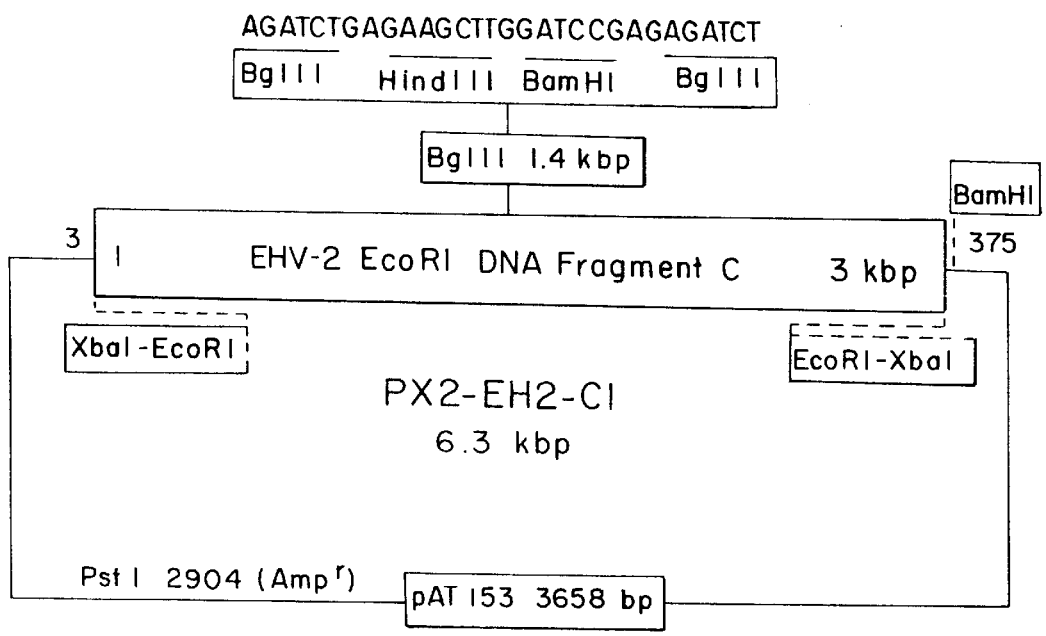

5.1.4. Restriction of the DNA of the recombinant plasmid pEH2-E-C with the restriction endonuclease BglII and insertion of a DNA linker which contains the recognition sequences for BglII-HindIII-BamHI-BglII. Establishment of the recombinant plasmid pX2-EH2-C1 (FIG. 2).

Figure 3:
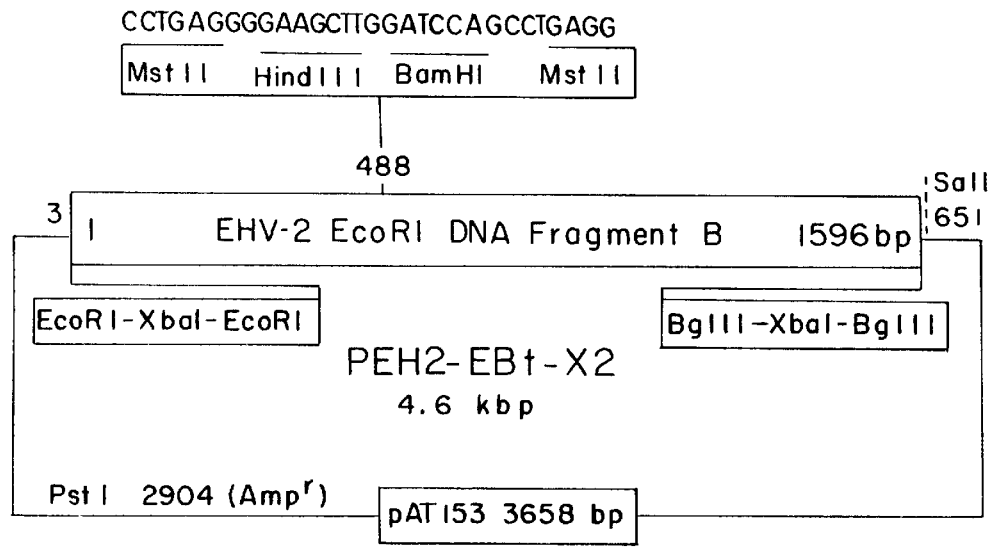

5.2 re Shuttle vector pEH2-EBt-X2:

The viral insert of the shuttle vector pEH2-EBt-X2 contains the DNA sequences of the right flank of the EcoRI DNA fragment B (1596 bp) into which a polylinker (MstII-HindIII-BamHI-MstII) has been inserted at nucleotide position 488 and likewise permits the insertion of foreign DNA elements (see FIG. 3).

The construction of the shuttle vector pEH2-EBt-X2 takes place in the following steps. The methods used are described in detail in Sambrook, Fritsch and Maniatis (1989), Molecular Cloning, Cold Spring Harbor, N.Y.

5.2.1. Molecular cloning of the right-hand terminus (1596 bp) of the EcoRI DNA fragment B (EcoRI/BglII) into the bacterial plasmid vector pAT153 into which a DNA linker with the cleavage sites for XbaI-EcoRI-BglII-XbaI has been inserted within the recognition sequences for EcoRI and SalI (pAT153 nucleotide position 3 to 650), the original recognition site for EcoRI in pAT153 having been eliminated. Establishment of the recombinant plasmid pEH2-EBt.

5.2.2. Characterisation of the right-hand terminus of the EcoRI DNA fragment B by determination of the DNA nucleotide sequence in the M13 phage system. The nucleotide sequence of the single-stranded DNA of the individual recombinant M13mp18 and 19 phages of the EcoRI DNA fragment B were determined by the dideoxy chain termination method with a modified T7 DNA polymerase (Sanger et al., 1977, Proc. Natl. Acad. Sci. USA 74: 5463–5467; Tabor and Richardson, 1987, proc. Natl. Acad. Sci. USA 74: 4767–4771). The DNA nucleotide sequence is depicted in FIG. 4.

5.2.3. Restriction of the DNA of the recombinant plasmid pEH2-E-Bt with the restriction endonuclease MstI (nucleotide position 488 of the EHV EcoRI DNA fragment B). Since there are no MstI cleavage sites present within the DNA sequences of pAT153, the recombinant plasmid is linearised by this treatment. Subsequently insertion of the DNA linker which contains the recognition sequences for MstI-HindIII-BamHI-MstI. Establishment of the recombinant plasmid pEH2-Ebt-X2 (FIG. 3).

6. Construction of a Recombinant Equine Herpesvirus Type 2 which Expresses Bacterial β-gelactosidase The bacterial β-galactosidase gene (LacZ) was chosen as foreign genetic information in order to demonstrate that the EHV-2 genome is able to function as eukaryotic vector and to express foreign genetic elements. The methods used are described in detail in Sambrook, Fritsch and Maniatis (1989), Molecular Cloning, Cold Spring Harbor, N.Y. The construction was carried out in the following steps:

6.1. The bacterial β-galactosidase gene (LacZ cassette; Hall et al., 1983, J. Mol. Appl. Gen 2: 101–106; Gorman et al., 1983, Science 221: 551–553) was isolated as HindIII/BamHI fragment from the recombinant plasmid pH-BB-LacZ (Rösen-Wolff et al., 1991, Virus Research, in the press).

Figure 5:
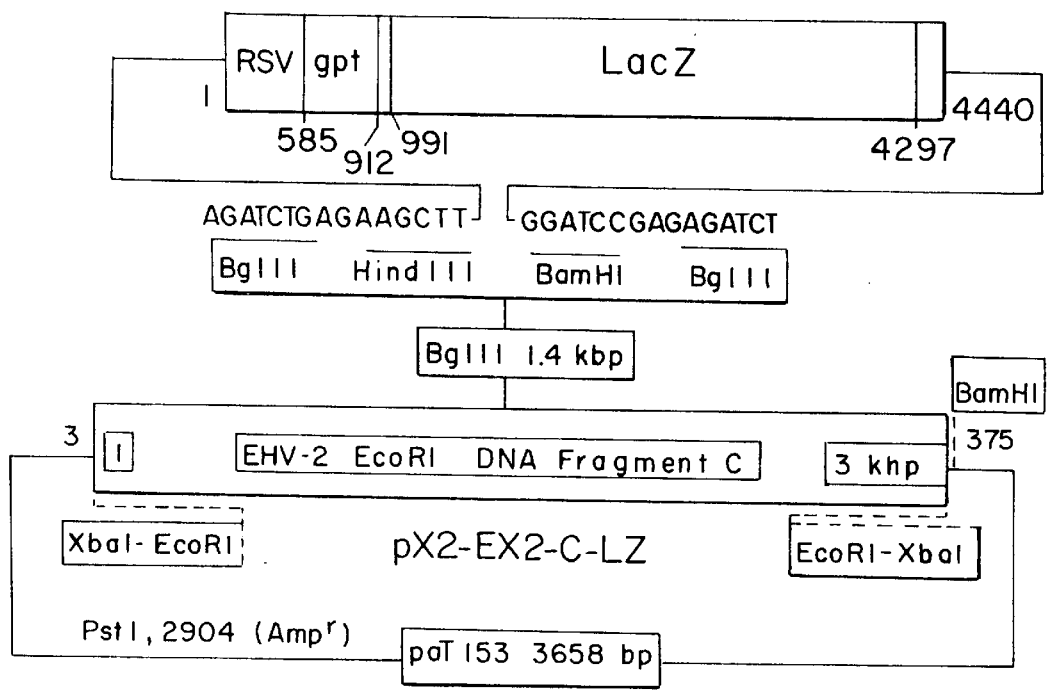

6.2. The LacZ casette was inserted into the HindIII and BamHI recognition sequence of the shuttle vector pC2-EH2-C1 (FIG. 2). The recombinant plasmid pX2-EH2-C-LZ (FIG. 5) results from insertion of the LacZ casette into the shuttle vector pX2-EH2-C1. This construct makes it possible to isolate the complete insert of the recombinant plasmid with the EHV-2 flanks and the LacZ cassette by treatment with the restruction endonuclease XbaI.

Figure 6:
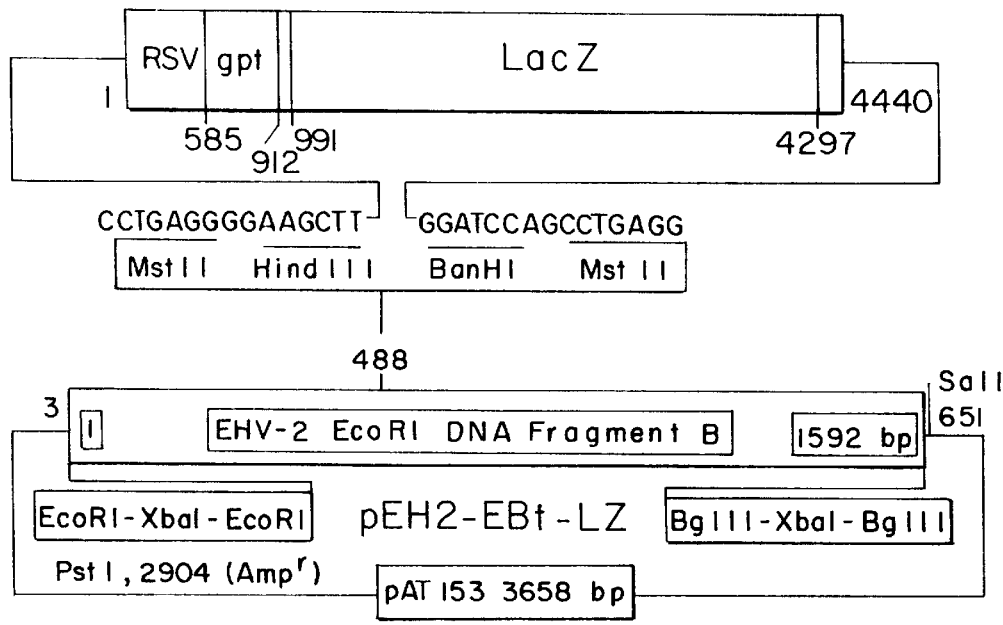

6.3. The LacZ cassette was inserted into the HindIII and BamHI recognition sequence of the shuttle vector pEH2-EBt-X2 (FIGS. 3) The recombinant plasmid pEH2-EBt-LZ (FIG. 6) results from insertion of the LacZ casette into the shuttle vector pEH2-EBt-X2. This construct makes it possible to isolate the complete insert of the recombinant plasmid with the EHV-2 flanks and the LacZ cassette by treatment with the restriction endonuclease XbaI.

6.4. Transfer of the LacZ cassette into the EHV-2 genome was carried out by DNA cotransfection as described by Sambrook, Fritsch and Maniatis (1989), Molecular Cloning, Cold Spring Harbor, N.Y. For the transfection, 1 to 3 picomole of DNA of the insert of the recombinant plasmid pX2-EH2-LZ or pEH2-Bt-LZ were coprecipitated with 0.01 to 0.1 picomole of native EHV-2 T400/3 DNA by the calcium phosphate method (Graham and van der Eb, 1973, Virology 52: 456–467).

6.5. The coprecipitated DNA was employed for transfection of ED cell cultures. The transfected cell cultures were incubated at 37° C. The transfected cells were investigated each day for the occurrence of cytopathic effects (CPE).

6.6. When CPE occurred, the virus recombinants was selected. The selection of those virus recombinants which express β-galactosidase was carried out by the blue plaque process. The transfected cell cultures which after the transfection harbour single virus plaques were covered with a layer of 1% agarose (supplied by BRL) in PBS which contained 250 μg/ml of the chromogenic substance 5-bromo-4-chloro-3-indolyl β-D-galactoside (X-Gal, supplied by Boehringer). Where there is β-galactosidase activity, X-Gal results in a blue colouration of the relevant visrus plaques within 4 to 8 hours.

Figure 7A:
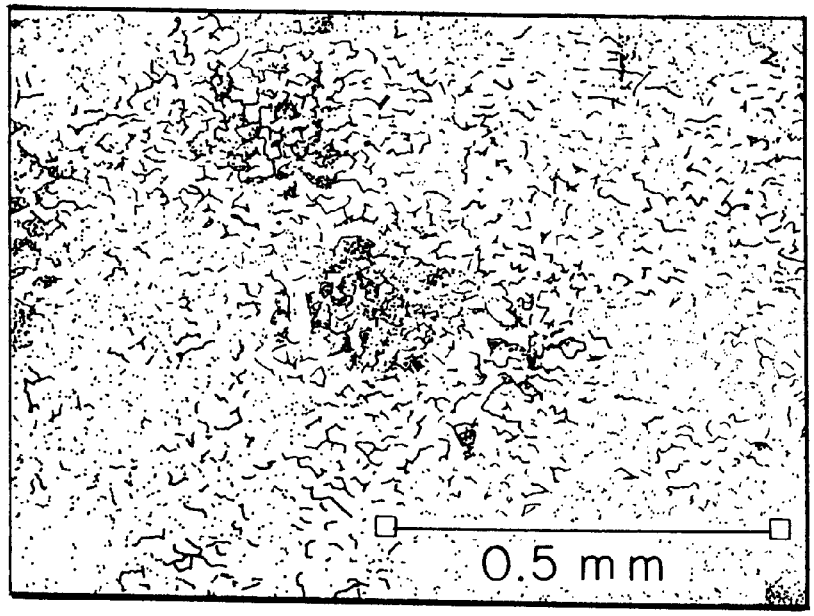
Figure 7B:
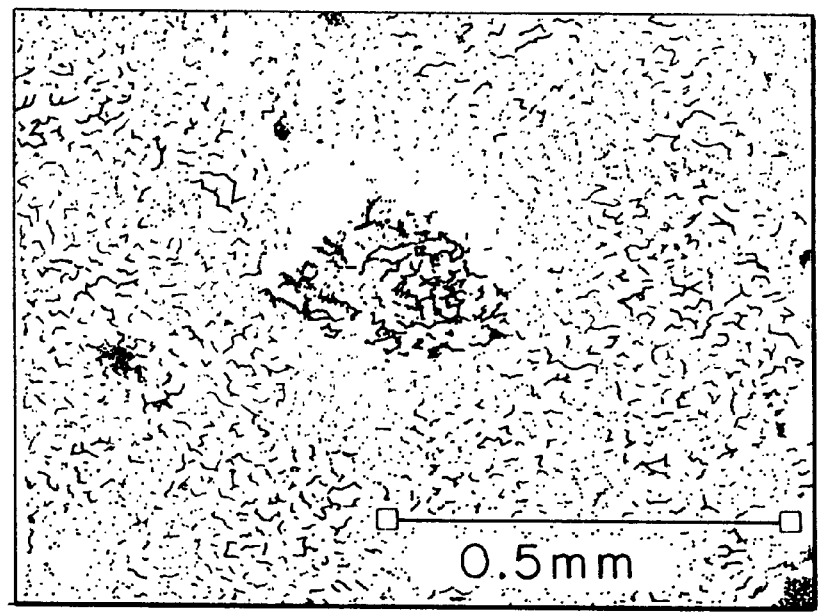
Figure 8:
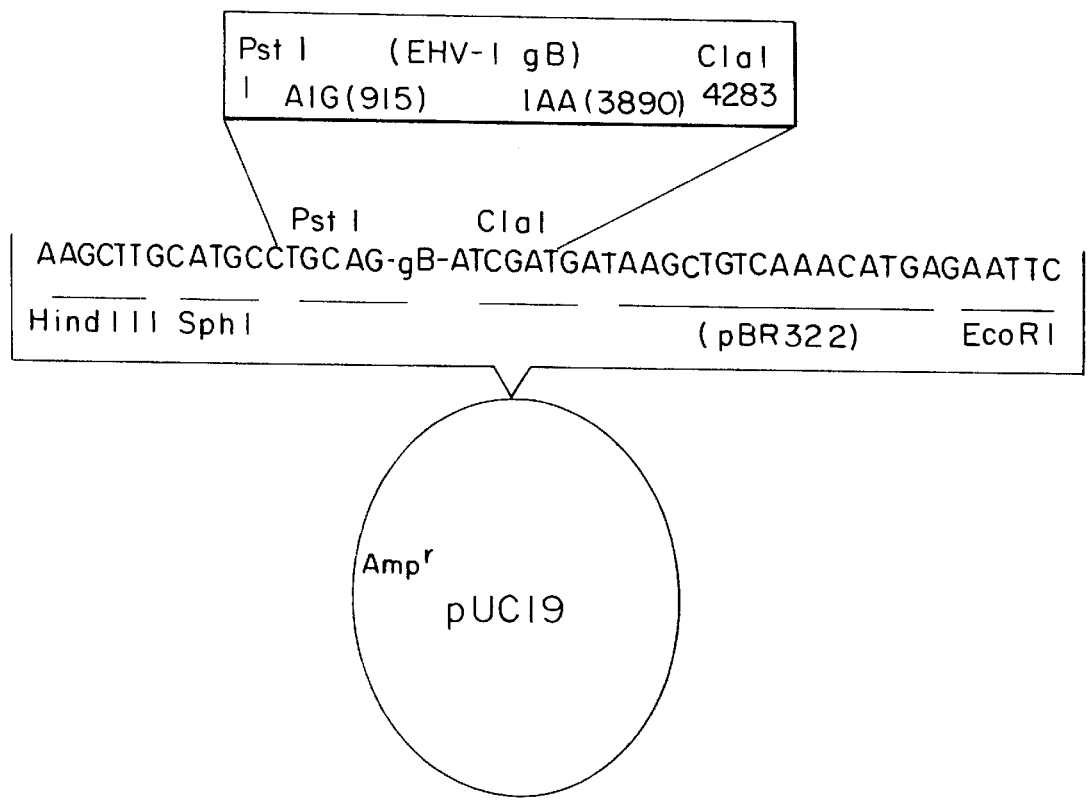

6.7. Individual blue plaques were picked out with a sterile glass cannula (diameter 1 mm) and cultured on ED cells. This procedure was repeated three times to purify recombinant virus strains. The DNA sequences of the β-galactosidase gene in the EHV-2 genome of the virus recombinants was detected by DNA/DNA hybridisations as described by Sambrook, Fritsch and Maniatis (1989), Molecular Cloning, Cold Spring Harbor, N.Y. This made it possible to establish the following recombinant virus strains:

6.7.1. Recombinant virus EHV-2-C-LacZ-658 which harbours the LacZ cassette in its genome within the DNA sequences of the EcoRI DNA fragment C of the EHV-2 genome and is able to express this foreign gene. The expression of β-galactosidase by the individual virus plaques can be detected as described in Section 6.6. by the blue coloration after treatment with X-Gal. An example is depicted in FIG. 7B.

6.7.2. Recombinant virus EHV-2-B-LacZ-231 which harbours the LacZ cassette in its genome within the DNA sequences of the EcoRI DNA fragment B of the EHV-2 genome and is able to express this foreign gene. The expression of β-galactosidase by the individual virus plaque can be detected as described in Section 6.6. by the blue coloration after treatment with X-Gal. An example is depicted in FIG. 7A.

7. Construction of EHV-2 Virus Recombinants which Contain the Gene for Glycoprotein gB of EHV-1.

7.1 Growing and purification of EHV-1 strain Mar87

Figure 9:
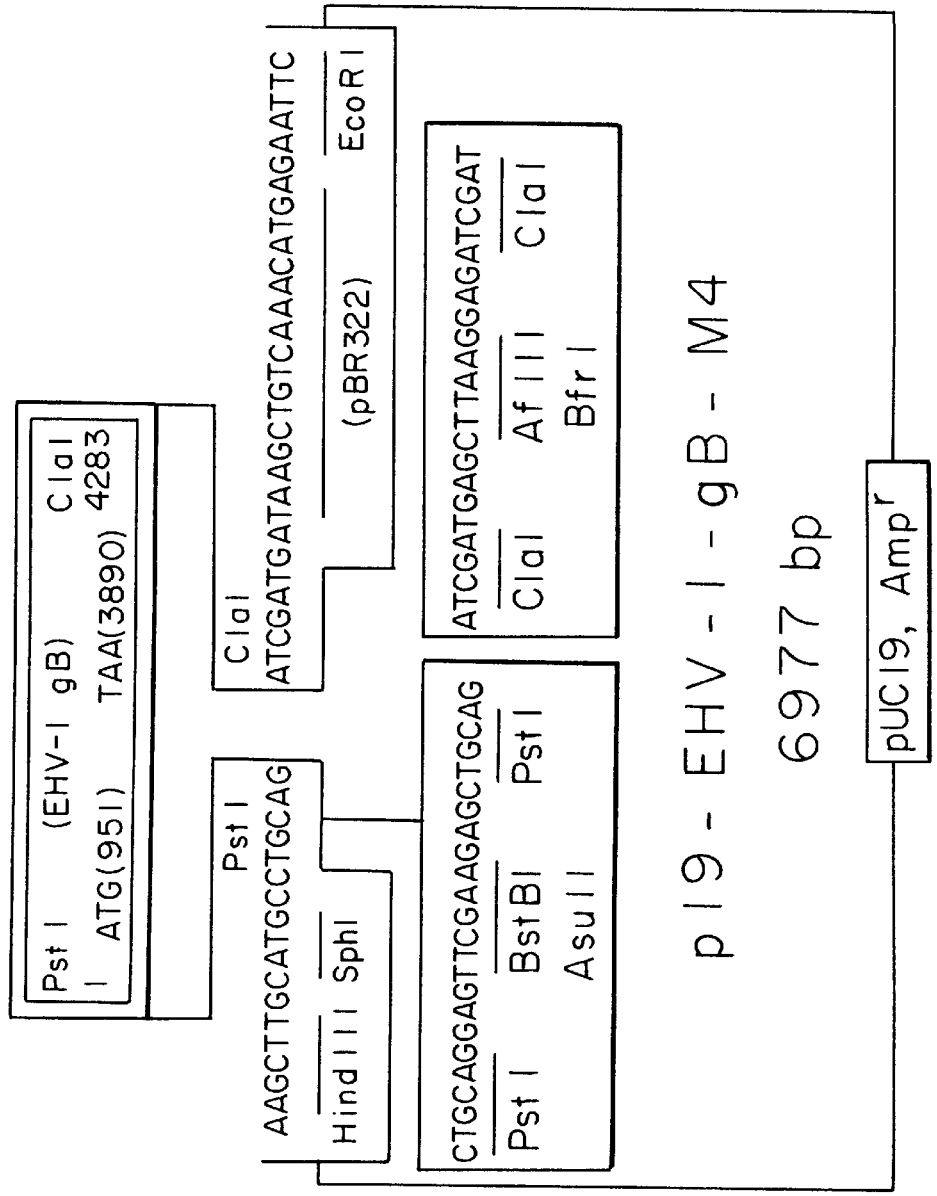

The strain Mar87 (deposited on 24.7.1990 at the Institut Pasteur C.N.C.M. under number I-980) was chosen as representative of EHV-1. The virus was grown on the permanent equine derm (ED) cell line in tissue culture at 37° C. The cell culture medium used was E-MEM (Virol. Arbeitsmethoden (Virol. Methods) vol. 1, Gustav Fischer Verlag, Stuttgart 1974, A. Mayr—P. A. Bachmann—B. Bibrack—G. Wittmann) which has been supplemented with 2.0 g of $NaHCO_3$ per litre and to which 10% FCS (fetal calf serum) has been added during cell growth. The virus-containing medium was harvested at 100% CPE and centrifuged at 5000×g to remove cell detritus. The virus particles were pelleted from the centrifugation supernatant at 25,000 rpm in a SW-27 rotor (supplied by Beckmann) in an ultracentrifuge for 1 hour. The virus pellet was resuspended in PBS (8 g of NaCl; 0.2 g of $K_2HPO_4$; 1.44 g of $Na_2HPO_4$; 0.2 g of KCl; (distilled water ad 1 litre) or in 1×TEN (50 mM Tris; 0.1 M NaCl; 1 mM EDTA; pH 7.2) and again pelleted by ultracentrifugation through a sucrose cushion (30% sucrose in PBS or 1×TEN) at 25,000 rpm in an SW-27 rotor for 1 hour and resuspended in 1×TEN.

7.2 Purification of the genomic DNA of EHV-1 and cloning of the BamHI DNA fragments A and I The virus particles resuspended in 1×TEN were lysed by addition of an aqueous 10% strength sodium dodecal sulphate solution (SDS), to a final SDS concentration of 1%, and viral protein was degraded after addition of proteinase K (supplied by Boehringer, final concentration 100 μg/ml) and incubation at 37° C. for 1 hour (Gross-Bellard et al., Eur. J. Biochem. 36, 32 ff). Extraction of the genomic DNA was carried out by extraction twice with phenol- and then with chloroform-isoamyl alcohol (Marmur 1961, J. Mol. Biol. 3, 208 ff). The aqueous supernatant was adjusted to 0.8 M potassium acetate, three times the volume of ethanol were added, and the mixture was stored at −20° C. overnight. After sedimentation of the precipitated DNA by centrifugation at 10,000×g, the DNA pellet was dissolved in 0.01×SSC or 0.1×SSC (1×SSC:0.15 M NaCl, 0.015 M Na citrate; pH 7.2).

The purified DNA of EHV-1 was restricted with the restriction enzyme BamHI in accordance with the manufacturer's (Boehringer Mannheim) statements, and the resulting DNA fragments were separated by electrophoresis in an agarose gel (80 V; 20 hours; 4° C.) (Sharp et al., 1973, Biochem. 12, 3055–3063). The DNA fragments BamHI-A (22 kb) and -I (7 kb) were isolated from the agarose gel by electroelution (Molecular Cloning; ed. Sambrook, Fritsch and Maniatis; Cold Spring Harbor, N.Y., 1989), and the two fragments each underwent molecular cloning (Molecular Cloning; ed. Sambrook, Fritsch and Maniatis; Cold Spring Harbor, N.Y., 1989) in the plasmid vector pAT153 (Twigg, A and Sheratt, 1980, Nature 283, 216–218) into the BamHI cleavage site of the vector.

7.3 Cloning of the gene from EHV-1 for the glycoprotein gB into pUC19

The terminal BamHI/PstI DNA fragment with 1388 bp of the BamHI fragment A of EHV-1 was isolated. For this, the DNA of the BamHI-A clone of EHV-1 was restricted with BamHI and PstI, the fragments were separated by electrophoresis in an agarose gel, and the DNA fragment with 1388 bp was obtained by electroelution (Molecular Cloning; ed. Sambrook, Fritsch and Maniatis; Cold Spring Harbor, N.Y., 1989). Likewise, the terminal BamHI/ClaI DNA fragment with 2901 bp of the BamHI fragment I of EHV-1 was isolated by incubation of the DNA of the BamHI-I clone of EHV-1 with the restriction enzymes BamHI and ClaI (Double Digest, Molecular Cloning; ed. Sambrook, Fritsch and Maniatis; Cold Spring Harbor, N.Y., 1989), electrophoretic fractionation of the resulting DNA fragments in an agarose gel and subsequent electroelution of the DNA fragment with 2901 bp.

The isolated DNA fragments were inserted into the plasmid vector pUC19 in such a way that the recombinant plasmid produced therefrom contained the intact gene for gB of EHV-1. For this, the DNA of the vector pUC19 was opened with EcoRI and PstI (Double Digest), and a chemically synthesised DNA adaptor with a terminal EcORI recognition sequence, with a terminal PstI recognition sequence and with an internal ClaI recognition sequence was inserted into the opened vector at the EcoRI and PstI cleavage site (Molecular Cloning; ed. Sambrook, Fritsch and Maniatis; Cold Spring Harbor, N.Y., 1989). The DNA of the plasmid vector modified in this way was in turn restricted with PstI and ClaI, and subsequently the opened plasmid DNA was incubated with the isolated BamHI/PstI DNA fragment (1388 bp) of the BamHI fragment A, with the isolated BamHI/ClaI DNA fragment (2901 bp) of the BamHI fragment I of EHV-1 and with the enzyme T4 ligase to insert the two EHV-1 DNA fragments (Molecular Cloning; ed. Sambrook, Fritsch and Maniatis; Cold Spring Harbor, N.Y., 1989). The recombinant plasmid, prepared in this way, with 6955 bp, which contains the intact gene for gB of EHV-1 as 4283 bp insert (ATG at position 915, TAA at position 3890) was called p19-EHV-1-GpB (see FIG. 8).

Subsequently a DNA adaptor with the doublestranded deoxyribonucleotide sequence with the following base sequence which is identified as SEQUENCE ID. NO. 20.

5'-GGAGTTCGAAGAGCTGCA-3'

3'-ACGTCCTCAAGCTTCTCG-5' with flanking PstI sites and internal BstBI (AusII) site was chemically synthesised into the recombinant plasmid p19-EHV-1-GpB and inserted into the PstI recognition sequence of the plasmid p19-EHV-1-GpB. For this, the plasmid was cut with PstI, and the linearised plasmid was incubated with the double-stranded DNA adaptor and T4 ligase.

A second double-stranded DNA adaptor with the nucleotide sequence which is identified as SEQUENCE ID. NO. 21.

5'-CGATGAGCTTAAGGAGAT-3'

3'-GACTCGAATTCCTCTAGC-5' with flanking ClaI sites and internal AflII (BfrI) site was chemically synthesised and inserted into the ClaI site of p19-EHV-1-GpB. For this, the plasmid provided with the first adaptor was treated with ClaI and subsequently incubated with the second double-stranded adaptor and T4 ligase. The newly produced plasmid was called p19-EHV-1-gB-M4 (FIG. 9).

7.4 Preparation of shuttle vectors for insertion of the gene for gB of EHV-1 into the genome of EHV-2

The double-stranded DNA sequence with the base sequence which is identified as SEQUENCE ID. NO. 22.

Figure 10:
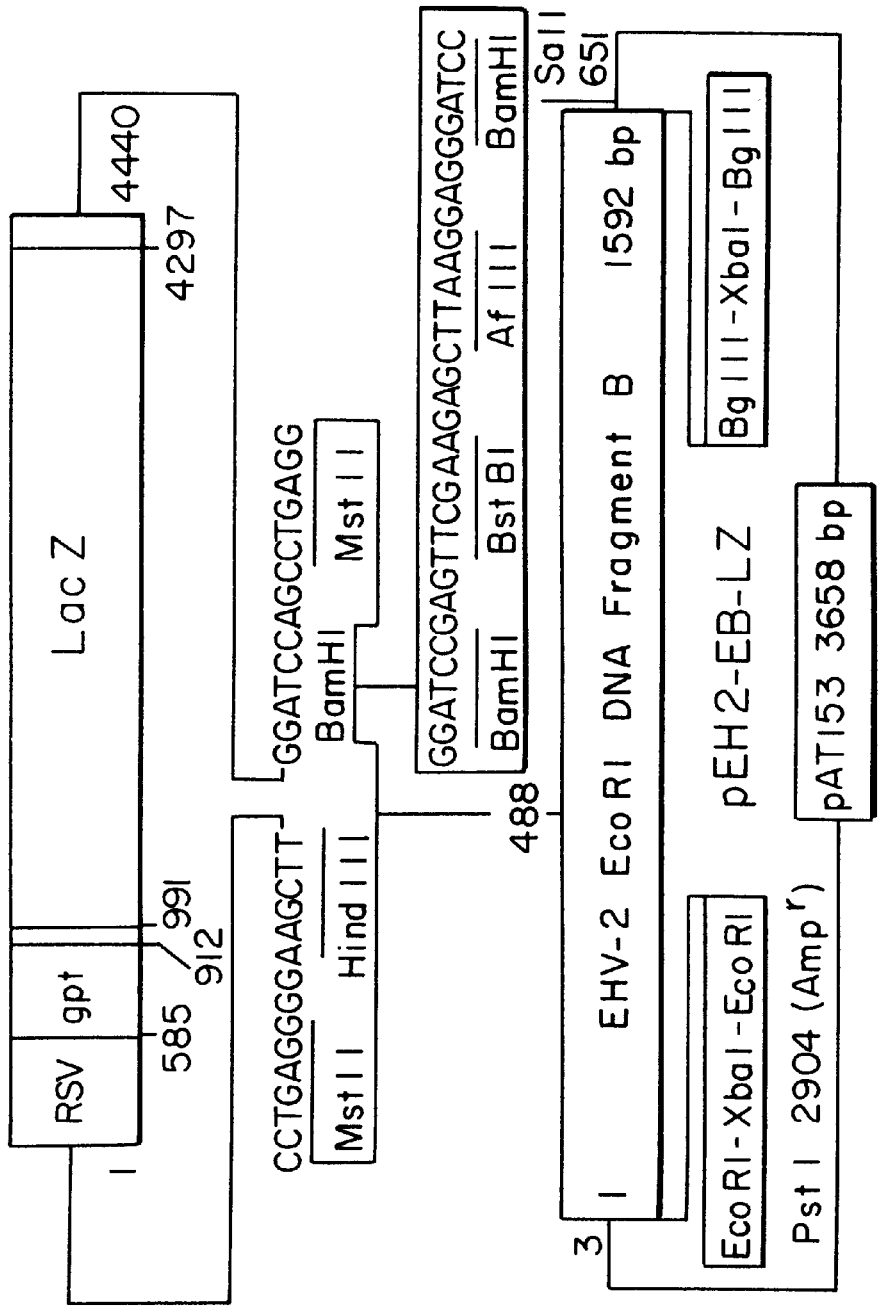

5'-GATCCGAGTTCGAAGAGCTTAAGGAGG-3'
3'-GCTCAAGCTTCTCGAATTCCTCCCTAG-5' with flanking BamHI sites and internal BstBI (AsuII) and BfrI (AflII) site was chemically synthesised and inserted as double-stranded DNA adaptor into the shuttle vector pEH2-EBt-LZ, which is described in Example 6.3 and already harboured the marker gene for lacZ, into the BamHI recognition sequence. For this, pEH2-EBt-LZ was treated with BamHI and subsequently incubated with T4 ligase and the double-stranded DNA adaptor described here. The result was the plasmid pEH2-EB-LZ (see FIG. 10).

Figure 11:
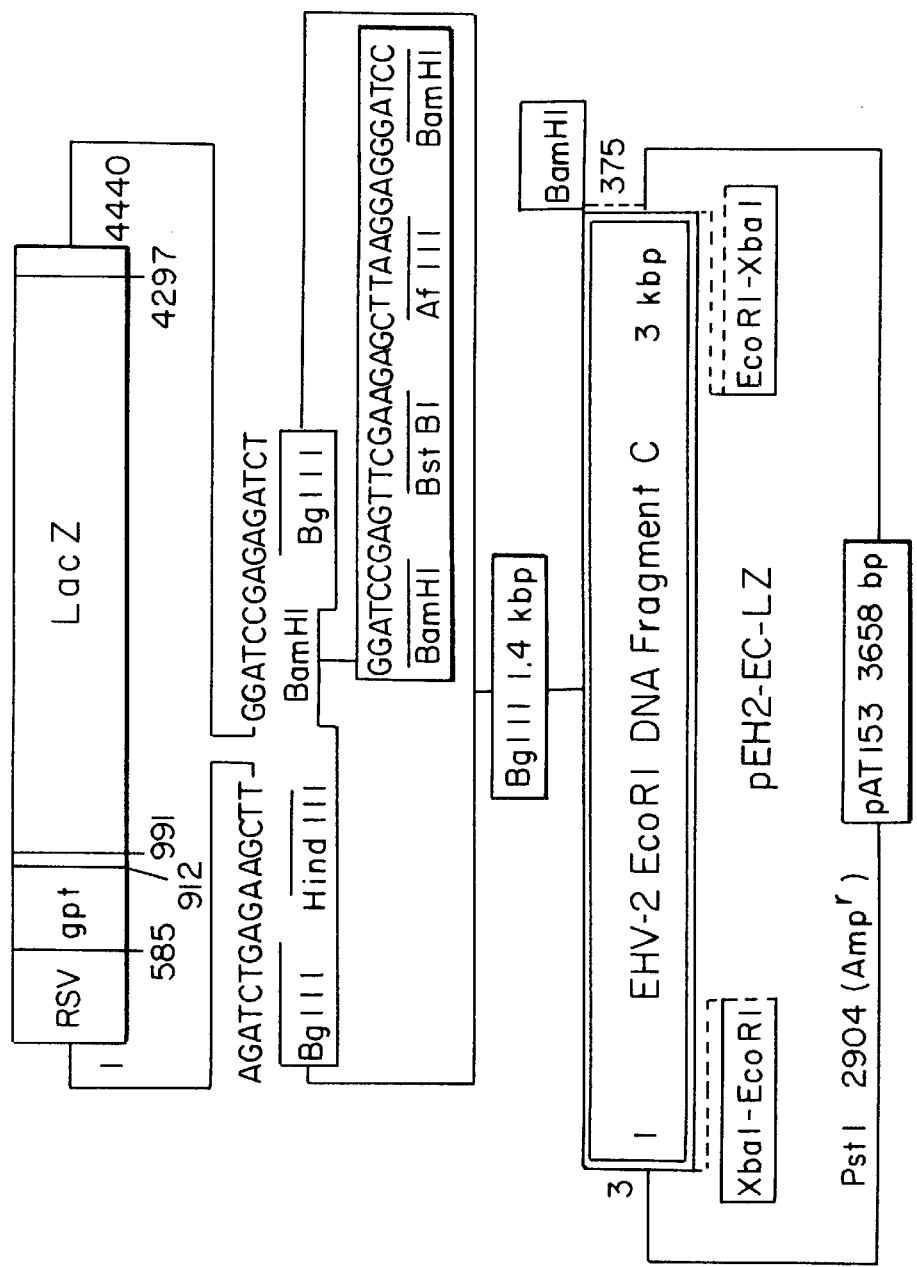

The same double-stranded DNA adaptor with flanking BamHI sites and internal BstBI (AsuII) and BfrI (AflII) site was inserted as double-stranded DNA adaptor into the BamHI site of the recombinant plasmid pX2-EH2-C-LZ (see Example 6.2 above) which already harboured the marker gene for lacz, by treatment of pX2-EH2-C-LZ with BamHI and subsequent incubation of the cut plasmid DNA with the synthetically prepared DNA sequence and T4 ligase. The result was the plasmid pEH2-EC-LZ (see FIG. 11).

The gene of EHV-1 for gB from p19-EHV-1-gB-M4 was isolated for insertion into the shuttle vectors pEH2-EC-LZ and pEH2-EB-LZ. For this, the plasmid p19-EHV-1-gB-M4 was treated with the restriction enzymes BstBI and BfrI in a double digest, and the resulting DNA fragments were separated by electrophoresis in an agarose gel (Sharp et al., 1973, Biochem. 12, 3055–3063). The DNA fragment with 4283 bp, which contains the gene for gB of EHV-1, was isolated from the gel by electroelution (Molecular Cloning; ed. Sambrook, Fritsch and Maniatis; Cold Spring Harbor, N.Y.; 1989).

Figure 12:
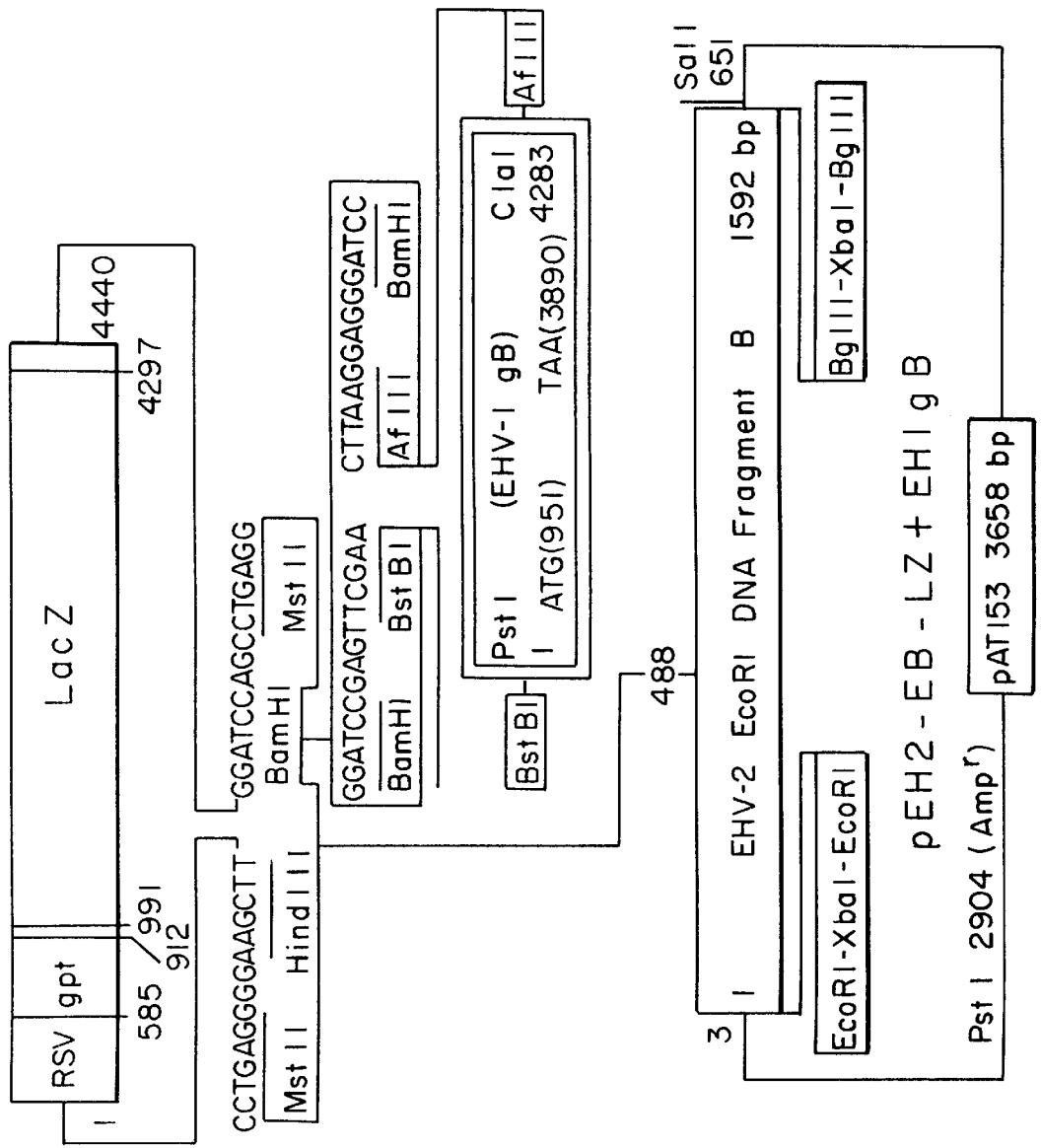

The 4283 bp DNA fragment with the gene for gB EHV-1 was now inserted in each case into the BstBI and BfrI recognition sequences of the two recombinant plasmids pEH2-EC-LZ and pEH2-EB-LZ. The DNA of the recombinant plasmid pEH2-EB-LZ was treated in a double digest with the restriction enzymes BstBI and BfrI. The restricted and thus linearised plasmid DNA was incubated with the 4.28 kbp DNA fragment and T4 ligase, and thus the gene for gB of EHV-1 was inserted. The result was the shuttle vector pEH2-EB-LZ+EH1gB (see FIG. 12 for transfer of the genes for gB of EHV-1 and lacZ from E.coli into the genome of EHV-2.

Figure 13:
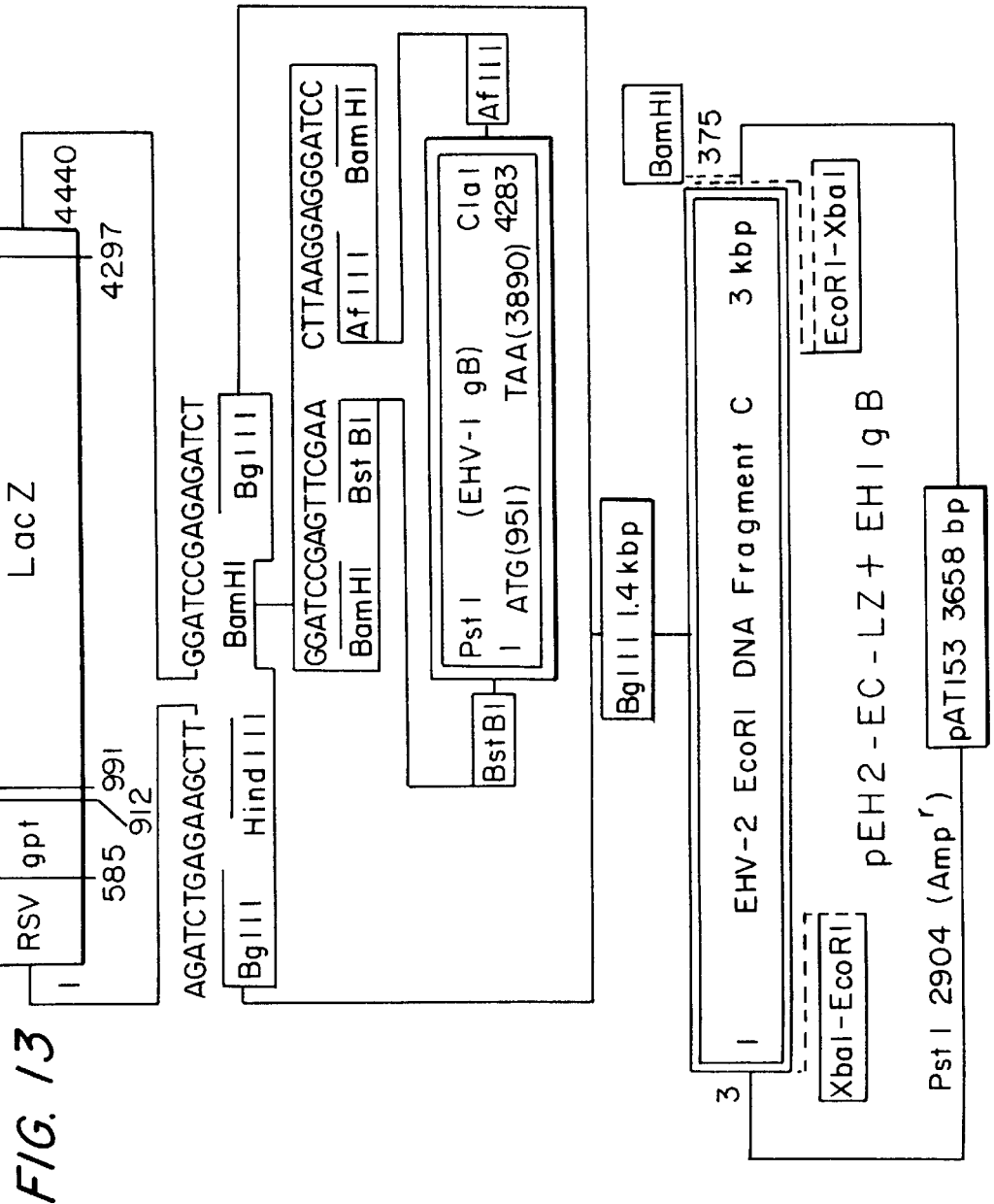

In a second approach, the DNA of the recombinant plasmid pEH2-EC-LZ was treated in a double digest with the restriction enzymes BstBI and BfrI. The restricted and thus linearised plasmid DNA was incubated with the 4.28 kbp DNA fragment described above and T4 ligase, and thus the gene for gB of EHV-1 was also inserted into this plasmid. The result was the second shuttle vector pEH2-EC-LZ+EH1gB (see FIG. 13, likewise for transfer of the genes for gB of EHV-1 and lacZ from E.coli into the genome of EHV-2.

7.5 Transfection experiments with EHV-2-T400 DNA and shuttle vector DNA for the preparation of EHV-2 recombinants which carry the genes for gB of EHV- and lacZ of E. coli The transfer of the LacZ gene and of the EHV-1-gB gene into the EHV-2 genome was carried out by DNA cotransfection.

For this, initially the DNA of the plasmid pEH2-EB-LZ+EH1gb was restricted with XbaI, and the resulting fragments were separated by electrophoresis in an agarose gel. The DNA fragment with 15 kb, which represented the insert, was electroeluted (Sambrook, Fritsch and Maniatis (1989), Molecular Cloning, Cold Spring Harbor, N.Y.).

Viral DNA of EHV-2 strain Thein 400/3 was isolated and purified in a CsCl gradient.

The cell monolayer of confluent ED cells cultivated in 24-well plates was washed twice with medium, once with medium supplemented with DEAE-dextran (MW 2,000,000, concentration 1 mg/ml), a further time with medium supplemented with DEAE-dextran (MW 2,000,000, concentration 0.1 mg/ml) and subsequently mixed with 100 $\mu$l of medium supplemented with DEAE-dextran (MW 2,000,000, concentration 0.05 mg/ml) per well.

In each case 1–3 pico mole of DNA of the insert of plasmid pEH2-EB-LZ+EH1gB in 15 $\mu$l in each case was added to the dextran-treated ED cells per well. In addition, 0.01 to 0.1 pico mole of the DNA of EHV-2 Thein 400/3 in 55 $\mu$l in each case was added to each well.

In a second approach, the dextran-treated ED cells were mixed with in each case 1–3 pico mole of DNA of the insert of plasmid pEH2-EC-LZ+EH1gB in 25 $\mu$l in each case and with in each case 0.01 to 0.1 pico mole of the DNA of EHV-2 Thein 400/3 in 55 $\mu$l in each case.

The cultures were incubated at 37° C. for 6 hours.

The transfected cell cultures were now incubated in medium which was supplemented with 5% FCS at 37° C. and tested each day for the occurrence of cytopathic effects (CPE).

When CPE occurred, the virus recombinants were selected. Virus recombinants which expressed $\beta$-galactosidase were selected by the blue plaque method. The transfected cell cultures which, after the transfection, sporadically formed virus plaques were covered with a layer of 1% agarose (supplied by BRL) in PBS which contained 250 $\mu$g/ml of the chromogenic substance 5-bromo-4-chloro-3-indolyl $\beta$-D-galactoside (X-Gal, supplied by Boehringer). When there is $\beta$-galactosidase activity, X-Gal results in a blue coloration of the relevant virus plaques within four to eight hours.

Single blue plaques were stabbed with a sterile glass cannula (diameter 1 mm) and transferred to ED cells. This procedure was repeated three times to purify recombinant virus strains.

The DNA sequences of the gB gene in the EHV-2 genome of the virus recombinants were detected by DNA/DNA hybridisations. For this, infected cells were transferred to nitrocellulose filters, lysed and fixed.

The EHV-1-gB specific probe was prepared in the following way: the DNA of the plasmid p19-EHV-1-gB-M4 was restricted with the enzymes PstI and ClaI in a double digest, the resulting DNA fragments were separated by electrophoresis in an agarose gel, and the DNA fragment with 4.28 kbp was isolated by electroelution from the gel. This isolated DNA was radioactively labelled with $32_p$ (method of Rigby et al., 1977, J. Mol. Biol. 114, 237–256) and employed in the hybridisation as probe for detecting DNA sequences of the gene for gB of EHV-1 in EHV-2 recombinants.

It was possible in this way to establish recombinant EHV-2 strains which, besides the marker gene (lacZ), also harbour the gene for gB of EHV-1. For example, it was possible with the aid of the shuttle vector pEH2-EC-LZ+EH1gB to construct the virus recombinants EH2LZgB4 and EH2LZgB3 which contained the gB gene of EHV-1.

EHV-2 recombinants which had been identified in this way and contained DNA sequences, detected by DNA/DNA hybridisation, of the gB gene of EHV-1 were again inoculated onto ED cells to form single plaques. The EHV-2 recombinants EH2LZgB45 and EH2LZgB123 were isolated in this way.

Transcription of the foreign DNA was carried out by means of DNA/RNA hybridisation. For this, ED cells were infected with the virus recombinants in an infection dose of 50 plaque-forming units (PFU)/cell. The RNA from these infected cells was extracted by means of guanidineHCl and caesium chloride by the method of Glisin et al (1974, Biochemistry 106, 492ff) and Ullrich et al (1977, Science 196, 1313ff). The subsequent analyses to determine the content of EHV-1-gB specific RNA by means of the above-mentioned EHV-1-gB specific DNA probe was by the method of Lehrach et al (Biochemistry 16, 4743–4751) and "Molecular Cloning", ed. Sambrook, Fritsch and Maniatis; Cold Spring Harbor, N.Y., 1989.

To detect EHV1-gB specific RNA, the insert of the plasmid P19-EHV1gBM4 was employed as probe. Using this method, it was possible to detect specific RNA transcripts in the ED cells which had been infected with virus recombinants EH2LZgB45 and EHVLZgB123. The translation of the foreign DNA was detected immunologically.

What is claimed is:

1. A replication-competent equine herpesvirus-2, which comprises genome fragment EcoRI-B or EcoRI-C, and wherein a foreign DNA sequence has been inserted into a restriction site within said genome fragment EcoRI-B or EcoRI-C which is capable of the foreign DNA uptake.

2. A replication competent herpesvirus-2 according to claim 1, which is nonvirulent or attenuated.

3. A replication competent equine herpesvirus-2 according to claim 1, wherein one or more segments of genome sequences not necessary for replication of said equine herpesvirus are absent from said equine herpesvirus.

4. A replication competent equine herpesvirus-2 according to claim 1, wherein said foreign DNA sequence encodes a protein.

5. A replication-competent equine herpesvirus-2 according to claim 1, which contains a repetitive DNA sequence into which there has been inserted a foreign DNA sequence, wherein said repetitive DNA sequence is contained in genome fragment EcoRI-B or genome fragment EcoRI-C of said equine herpesvirus-2, said repetitive DNA sequence in said genome fragment EcoRI-B contains a MstII site, or said repetitive DNA sequence in said genome fragment EcoRI-C contains a BglII site, and said foreign DNA sequence is inserted at said MstII site of said genome fragment EcoRI-B or at said BglII site of said genome fragment EcoRI-C.

6. A process for preparing a replication-competent equine herpesvirus-2 according to claim 1 which comprises:
  a) identifying an insertion site in said genome fragment EcoRI-B or EcoRI-C by digesting said genome fragment with a restriction enzyme;
  b) inserting a foreign DNA sequence into said insertion site;
  c) cloning said genome fragment containing said foreign DNA sequence into a shuttle vector;
  d1) co-transfecting cell suitable for virus growth with said shuttle vector together with a native equine herpesvirus, or
  d2) transfecting said shuttle vector into suitable host cells and infecting said host cell with a native equineherpes virus, or
  d3) infecting suitable host cell with a native equine herpesvirus and transfecting said shuttle vector into said host cells; and
  e) isolating and growing equine herpesvirus-2 recombinants obtained after d1), d2) or d3).

7. The process according to claim 6 wherein the genome fragment as recited in a) is contained in a vector.

8. A shuttle vector comprising a foreign DNA sequence inserted into a restriction site within genome fragment EcoRI-B or EcoRI-C of a replication-competent equine herpesvirus-2.

9. A shuttle vector according to claim 8, which contains a repetitive DNA sequence into which there has been inserted a foreign DNA sequence, wherein said repetitive DNA sequence is contained in genome fragment EcoRI-B or genome fragment EcoRI-C of said equine herpesvirus-2, said repetitive DNA sequence in said genome fragment EcoRI-B contains a MstII site, or said repetitive DNA sequence in said genome fragment EcoRI-C contains a BglII site, and said foreign DNA sequence is inserted at said MstII site of said genome fragment EcoRI-B or at said BglII site of said genome fragment EcoRI-C.

\* \* \* \* \*

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
(A) LENGTH: 18 Nucleotides
(B) TYPE: Nucleic Acid
(C) STRANDEDNESS: Both
(D) TOPOLOGY: Linear (xi) SEQUENCE DESCRIPTION: SEQ ID NO: 1:

GGAGTTCGAA GAGCTGCA 18

(2) INFORMATION FOR SEQ ID NO: 2:

(i) SEQUENCE CHARACTERISTICS:
(A) LENGTH: 18 Nucleotides
(B) TYPE: Nucleic Acid
(C) STRANDEDNESS: Both
(D) TOPOLOGY: Linear (xi) SEQUENCE DESCRIPTION: SEQ ID NO: 2:

GCTCTTCGAA CTCCTGCA 18

(2) INFORMATION FOR SEQ ID NO: 3:

(i) SEQUENCE CHARACTERISTICS:
(A) LENGTH: 18 Nucleotides
(B) TYPE: Nucleic Acid
(C) STRANDEDNESS: Both
(D) TOPOLOGY: Linear (xi) SEQUENCE DESCRIPTION: SEQ ID NO: 3:

CGATGAGCTT AAGGAGAT 18

(2) INFORMATION FOR SEQ ID NO: 4:

(i) SEQUENCE CHARACTERISTICS:
(A) LENGTH: 18 Nucleotides
(B) TYPE: Nucleic Acid
(C) STRANDEDNESS: Both
(D) TOPOLOGY: Linear (xi) SEQUENCE DESCRIPTION: SEQ ID NO: 4:

CGATCTCCTT AAGCTCAG 18

(2) INFORMATION FOR SEQ ID NO: 5:

(i) SEQUENCE CHARACTERISTICS:
        (A) LENGTH: 27 Nucleotides
        (B) TYPE: Nucleic Acid
        (C) STRANDEDNESS: Double
        (D) TOPOLOGY: Linear (xi) SEQUENCE DESCRIPTION: SEQ ID NO: 5:

GATCCGAGTT CGAAGAGCTT AAGGAGG                                           27

(2) INFORMATION FOR SEQ ID NO: 6:

(i) SEQUENCE CHARACTERISTICS:
        (A) LENGTH: 30 Nucleotides
        (B) TYPE: Nucleic Acid
        (C) STRANDEDNESS: Double
        (D) TOPOLOGY: Linear (xi) SEQUENCE DESCRIPTION: SEQ ID NO: 6:

AGATCTGAGA AGCTTGGATC CGAGAGATCT                                        30

(2) INFORMATION FOR SEQ ID NO: 7:

(i) SEQUENCE CHARACTERISTICS:
        (A) LENGTH: 30 Nucleotides
        (B) TYPE: Nucleic Acid
        (C) STRANDEDNESS: Double
        (D) TOPOLOGY: Linear (xi) SEQUENCE DESCRIPTION: SEQ ID NO: 7:

CCTGAGGGGA AGCTTGGATC CAGCCTGAGG                                        30

(2) INFORMATION FOR SEQ ID NO: 8:

(i) SEQUENCE CHARACTERISTICS:
        (A) LENGTH: 1596 Nucleotides
        (B) TYPE: Nucleic Acid
        (C) STRANDEDNESS: Double
        (D) TOPOLOGY: Linear (xi) SEQUENCE DESCRIPTION: SEQ ID NO: 8:

AATTCCCCC CCTCCCGCTG CCTCTTAATA TAACCCGTGT                               40

GGAGGGGGAT GCGACGGATG CCCCGAGCGG GCGGGCTCGC                              80

GCGCGCGCTC TCTATTGGCA AAACAAAAGC AGTAGGCAAG                              120

TAAACCCCCG CTCCCCTCGA GCTCACCTGC AACCTCGCTT                              160

GTTGCAAAGA TAGATGGAGT GCTGGGTGAG CTCAGCAGAG                              200

GCTATCCTCA ATTCTTATGG AGGTGCAGTT TCCAGCTGAG                              240

GCCCATGGTC CTCGAGATGT GCCTCAGCAT CCTATTTTTT                              280

AGTTTTCTGT TTCTGTGAGC CACCGAAGAG AGAAAAGTCA                              320

TAAAGTTGGC ATTCCTTCCC AGCTCATCCA ATCGCACCTT                              360

CTTCTTGTCG CAGAGGATCT TGGGTATCAG GTTGCACTTC                              400

TTGTAGCCCA GGACCGCGCA CTCGTGTTTG TTCTTGGTGT                              440

GGCTGATGAT CCTCTTGGAG AAGTCAAAGT ATCCCCCCCT                              480

AGCGAGCCTG AGGACGGCGC GCACGTCCAG CCTCCCGAAG                              520

GAGGCGCACT CGTACAGGCA CTCCAGGAAC CGCTTGGTAT                              560

GGTCTGGATC TGGGCCTTGT TGCGCGTCTC CACCGTGGAG                              600

AAGATGGCGT TCTTGACCAG GTTGAGCCTG GCGCGCGGGT                              640

| | |
|---|---|
| TGGTCAGTAT GGGCGCGGTC TCGCTGTAGA CGCGAGCCAC | 680 |
| CAGCCCGGGG CCGTGCACCT TGGAGATGGT GGCGGTGGCC | 720 |
| GCCTTGAACC AGGACACGTT GGAGCCCCTC TGGGTGGAGA | 760 |
| CTGGCCGAGG GGAAGTTGGT GGTCCAGAAG ACGTCGCTCC | 800 |
| TCCCCCGGCG CACCAGCTGC TGGTTCTCCA GGCCCTGCAG | 840 |
| GTCCAGGGTG GAGTTCCAGT TGGCCACGGA GATGGGAAAG | 880 |
| ACCGTGCGCA CGGGCATGAA GCACTTGAGG TTGCCCACGG | 920 |
| CGTAGAGGAA GGACAGGTAG TCCCCGCTGA TGTTCATGTT | 960 |
| GATGGCCGTG CCGCTGGCGC ACGCCGCGTC CGAGTAGAAC | 1000 |
| ACGCTCACGG TGAAGGAGGG CTCCTTCACG GAGTACTTTC | 1040 |
| TGATCACAAA GTTGTTGGTG AGCCGGGGGA TGTCCATGAC | 1080 |
| GGTGCGGTAG CGGGCGCCGC GGGGGTCGCA CGCGATCTTG | 1120 |
| GTGTTGATGA CCATGTTGGT GTTGAACACG TTGATCCCGA | 1160 |
| ACCCGTGCAC CGAGAGGCTG CTCACCGGGG CGAAGCTGTC | 1200 |
| TGCCAGGGGG CGCCGTCTCT CCCCCGACCC AAAGAGCGCC | 1240 |
| CCCTCGCGGA GACCCAGCGG CAGCGTCATG GTGGCCCGGG | 1280 |
| TCTCCCGGGG GGCATGTACT TGCCCCTGTT GAGCAGGGAG | 1320 |
| ACCAGTGCGT GGGCAGCCGG GCCCTCGCTC GAGGGCGGGC | 1360 |
| GCCTCGGACG GACGTGCCGC GCGCCCGGCC CATGGCCGCC | 1400 |
| AGACACATGG TGATCCTGTA GACGGCCATG CGCGGCGGGT | 1440 |
| ACACGTACCA GCGCTCTACG CCGCCCCCCT CCCTGGCGAC | 1480 |
| CACCCTGCCC GGTCTGGCGC CGGGGTCCTT CTTGTAGACC | 1520 |
| GCCACCTTGA GATAGGGCAT GGCCATGCTC ACGAGCGCCT | 1560 |
| GGTTCTCGTG AAAGCCCTCG GCCTCCAGGG AGATCT | 1596 |

(2) INFORMATION FOR SEQ ID NO: 9:

(i) SEQUENCE CHARACTERISTICS:
        (A) LENGTH: 15 Nucleotides
        (B) TYPE: Nucleic Acid
        (C) STRANDEDNESS: Double
        (D) TOPOLOGY: Linear (xi) SEQUENCE DESCRIPTION: SEQ ID NO: 9:

| | |
|---|---|
| AGATCTGAGA AGCTT | 15 |

(2) INFORMATION FOR SEQ ID NO: 10:

(i) SEQUENCE CHARACTERISTICS:
        (A) LENGTH: 15 Nucleotides
        (B) TYPE: Nucleic Acid
        (C) STRANDEDNESS: Double
        (D) TOPOLOGY: Linear (xi) SEQUENCE DESCRIPTION: SEQ ID NO: 10:

| | |
|---|---|
| GGATCCGAGA GATCT | 15 |

(2) INFORMATION FOR SEQ ID NO: 11:

(i) SEQUENCE CHARACTERISTICS:
        (A) LENGTH: 15 Nucleotides (B) TYPE: Nucleic Acid
        (C) STRANDEDNESS: Double
        (D) TOPOLOGY: Linear (xi) SEQUENCE DESCRIPTION: SEQ ID NO: 11:

CCTGAGGGGA AGCTT                                                        15

(2) INFORMATION FOR SEQ ID NO: 12:

(i) SEQUENCE CHARACTERISTICS:
        (A) LENGTH: 15 Nucleotides
        (B) TYPE: Nucleic Acid
        (C) STRANDEDNESS: Double
        (D) TOPOLOGY: Linear (xi) SEQUENCE DESCRIPTION: SEQ ID NO: 12:

GGATCCAGCC TGAGG                                                        15

(2) INFORMATION FOR SEQ ID NO: 13:

(i) SEQUENCE CHARACTERISTICS:
        (A) LENGTH: 18 Nucleotides
        (B) TYPE: Nucleic Acid
        (C) STRANDEDNESS: Double
        (D) TOPOLOGY: Linear (xi) SEQUENCE DESCRIPTION: SEQ ID NO: 13:

AAGCTTGCAT GCCTGCAG                                                     18

(2) INFORMATION FOR SEQ ID NO: 14:

(i) SEQUENCE CHARACTERISTICS:
        (A) LENGTH: 31 Nucleotides
        (B) TYPE: Nucleic Acid
        (C) STRANDEDNESS: Double
        (D) TOPOLOGY: Linear (xi) SEQUENCE DESCRIPTION: SEQ ID NO: 14:

ATCGATGATA AGCTGTCAAA CATGAGAATT C                                      31

(2) INFORMATION FOR SEQ ID NO: 15:

(i) SEQUENCE CHARACTERISTICS:
        (A) LENGTH: 24 Nucleotides
        (B) TYPE: Nucleic Acid
        (C) STRANDEDNESS: Double
        (D) TOPOLOGY: Linear (xi) SEQUENCE DESCRIPTION: SEQ ID NO: 15:

CTGCAGGAGT TCGAAGAGCT GCAG                                              24

(2) INFORMATION FOR SEQ ID NO: 16:

(i) SEQUENCE CHARACTERISTICS:
        (A) LENGTH: 24 Nucleotides
        (B) TYPE: Nucleic Acid
        (C) STRANDEDNESS: Double
        (D) TOPOLOGY: Linear (xi) SEQUENCE DESCRIPTION: SEQ ID NO: 16:

ATCGATGAGC TTAAGGAGAT CGAT                                              24

(2) INFORMATION FOR SEQ ID NO: 17:

(i) SEQUENCE CHARACTERISTICS:
        (A) LENGTH: 33 Nucleotides
        (B) TYPE: Nucleic Acid (C) STRANDEDNESS: Double
            (D) TOPOLOGY: Linear (xi) SEQUENCE DESCRIPTION: SEQ ID NO: 17:

GGATCCGAGT TCGAAGAGCT TAAGGAGGGA TCC                                33

(2) INFORMATION FOR SEQ ID NO: 18:

(i) SEQUENCE CHARACTERISTICS:
            (A) LENGTH: 15 Nucleotides
            (B) TYPE: Nucleic Acid
            (C) STRANDEDNESS: Double
            (D) TOPOLOGY: Linear (xi) SEQUENCE DESCRIPTION: SEQ ID NO: 18:

GGATCCGAGT TCGAA                                                    15

(2) INFORMATION FOR SEQ ID NO: 19:

(i) SEQUENCE CHARACTERISTICS:
            (A) LENGTH: 15 Nucleotides
            (B) TYPE: Nucleic Acid
            (C) STRANDEDNESS: Double
            (D) TOPOLOGY: Linear (xi) SEQUENCE DESCRIPTION: SEQ ID NO: 19

CTTAAGGAGG GATCC                                                    15

(2) INFORMATION FOR SEQ ID NO: 20:

(i) SEQUENCE CHARACTERISTICS:
            (A) LENGTH: 18 Nucleotides
            (B) TYPE: Nucleic Acid
            (C) STRANDEDNESS: Double
            (D) TOPOLOGY: Linear (xi) SEQUENCE DESCRIPTION: SEQ ID NO: 20:

GGAGTTCGAA GAGCTGCA                                                 18

(2) INFORMATION FOR SEQ ID NO: 21:

(i) SEQUENCE CHARACTERISTICS:
            (A) LENGTH: 18 Nucleotides
            (B) TYPE: Nucleic Acid
            (C) STRANDEDNESS: Double
            (D) TOPOLOGY: Linear (xi) SEQUENCE DESCRIPTION: SEQ ID NO: 21:

CGATGAGCTT AAGGAGAT                                                 18

(2) INFORMATION FOR SEQ ID NO: 22:

(i) SEQUENCE CHARACTERISTICS:
            (A) LENGTH: 27 Nucleotides
            (B) TYPE: Nucleic Acid
            (C) STRANDEDNESS: Double
            (D) TOPOLOGY: Linear (xi) SEQUENCE DESCRIPTION: SEQ ID NO: 22:

GATCCGAGTT CGAAGAGCTT AAGGAGG                                       27